(12) United States Patent
Souter et al.

(10) Patent No.: US 10,266,796 B2
(45) Date of Patent: *Apr. 23, 2019

(54) DETERGENT COMPOSITION

(71) Applicant: The Procter & Gamble Company, Cincinnati, OH (US)

(72) Inventors: Philip Frank Souter, Northumberland (GB); Alan Thomas Brooker, Newcastle upon Tyne (GB); Colin Ure, Tune&Wear (GB); Craig Adam Wilkinson, Newcastle upon Tyne (GB); Lindsay Suzanne Bewick, Newcastle upon Tyne (GB); Kelly Ann Millward, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 33 days.

This patent is subject to a terminal disclaimer.

(21) Appl. No.: 14/961,924

(22) Filed: Dec. 8, 2015

(65) Prior Publication Data

US 2016/0177237 A1 Jun. 23, 2016

(30) Foreign Application Priority Data

Dec. 17, 2014 (EP) .................................... 14198695

(51) Int. Cl.
*C12N 9/50* (2006.01)
*C11D 3/386* (2006.01)
*C11D 1/12* (2006.01)
*C11D 17/04* (2006.01)
*C12N 9/28* (2006.01)
*C11D 1/14* (2006.01)
*C11D 1/75* (2006.01)

(52) U.S. Cl.
CPC ............... *C11D 3/386* (2013.01); *C11D 1/12* (2013.01); *C11D 1/146* (2013.01); *C11D 1/75* (2013.01); *C11D 3/38681* (2013.01); *C11D 17/041* (2013.01); *C12N 9/2417* (2013.01); *C12Y 302/01001* (2013.01)

(58) Field of Classification Search
CPC ..................... C11D 3/38609; C11D 3/38627
USPC .......................................... 510/226; 435/219
See application file for complete search history.

(56) References Cited

U.S. PATENT DOCUMENTS

| | | |
|---|---|---|
| 3,308,067 A | 3/1967 | Diehl |
| 3,629,121 A | 12/1971 | Eldib |
| 3,723,322 A | 3/1973 | Diehl |
| 3,803,285 A | 4/1974 | Jensen |
| 3,929,107 A | 12/1975 | Renger |
| 3,933,672 A | 10/1976 | Bartlolotta et al. |
| 4,136,045 A | 1/1979 | Gault et al. |
| 4,141,841 A | 2/1979 | McDanald |
| 4,379,080 A | 4/1983 | Murphy |
| 4,689,167 A | 8/1987 | Collins et al. |
| 4,765,916 A | 8/1988 | Ogar et al. |
| 4,824,599 A | 4/1989 | de Jong et al. |
| 4,972,017 A | 11/1990 | Smith et al. |
| 4,972,047 A | 11/1990 | Puddle et al. |
| 5,035,661 A | 7/1991 | Steinhardt et al. |
| 5,288,627 A | 2/1994 | Nelsen et al. |
| 5,308,532 A | 5/1994 | Adler et al. |
| 5,453,216 A | 9/1995 | Kellett |
| 5,695,679 A | 12/1997 | Christie et al. |
| 5,698,507 A | 12/1997 | Gorlin et al. |
| 5,763,385 A | 6/1998 | Bott et al. |
| 5,766,371 A | 6/1998 | Bunch et al. |
| 5,804,542 A | 9/1998 | Scheper et al. |
| 5,853,430 A | 12/1998 | Shindo et al. |
| 5,856,164 A | 1/1999 | Outtrup et al. |
| 5,958,858 A | 9/1999 | Bettiol et al. |
| 6,103,683 A | 8/2000 | Romano et al. |
| 6,426,229 B1 | 7/2002 | Yamamoto et al. |
| 6,448,212 B1 | 9/2002 | Holderbaum et al. |
| 6,492,316 B1 | 12/2002 | Herbots et al. |
| 6,727,215 B2 | 4/2004 | Roberts et al. |
| 6,762,039 B2 | 7/2004 | Estell |
| 6,835,703 B1 | 12/2004 | Cho et al. |
| 7,432,099 B2 | 10/2008 | Andersen et al. |
| 7,445,644 B2 | 11/2008 | Song et al. |
| 7,541,026 B2 | 6/2009 | Power et al. |
| 8,012,267 B2 | 9/2011 | Jekel et al. |
| 8,163,686 B2 | 4/2012 | Gibis et al. |
| 8,173,587 B2 | 5/2012 | Preuschen |
| 8,399,396 B2 | 3/2013 | Gardner et al. |
| 8,431,517 B2 | 4/2013 | Song |
| 8,546,121 B2 | 10/2013 | Aehle et al. |
| 8,569,034 B2 | 10/2013 | Estell et al. |

(Continued)

FOREIGN PATENT DOCUMENTS

| | | |
|---|---|---|
| EP | 193360 B1 | 1/1991 |
| EP | 1288282 A1 | 3/2003 |

(Continued)

OTHER PUBLICATIONS

U.S. Appl. No. 14/961,914, filed Dec. 8, 2015, Brooker et al.
U.S. Appl. No. 14/961,915, filed Dec. 8, 2016, Brooker et al.
U.S. Appl. No. 14/961,919, filed Dec. 8, 2015, Souter et al.
U.S. Appl. No. 14/961,927, filed Dec. 8, 2015, Souter et al.
U.S. Appl. No. 14/961,931, filed Dec. 8, 2015, Souter et al.

(Continued)

*Primary Examiner* — Tekchand Saidha
(74) *Attorney, Agent, or Firm* — John T. Dipre

(57) ABSTRACT

Low-pH automatic dishwashing detergent composition comprising a low temperature amylase and a lime soap dispersing agent and wherein the composition has a pH as measured in 1% weight aqueous solution at 25° C. of from about 5 to about 7.5, preferably less than 6.9.

13 Claims, No Drawings

Specification includes a Sequence Listing.

(56) References Cited

U.S. PATENT DOCUMENTS

| | | |
|---|---|---|
| 8,841,247 B2 | 9/2014 | Miracle et al. |
| 9,136,955 B2 | 9/2015 | Robert et al. |
| 9,175,251 B2 * | 11/2015 | Dirr .................. C11D 1/721 |
| 9,550,964 B2 | 1/2017 | Miracle et al. |
| 9,738,754 B2 * | 8/2017 | Ebert ................ C08G 65/2624 |
| 10,081,782 B2 | 9/2018 | Brooker et al. |
| 2002/0198125 A1 | 12/2002 | Jones |
| 2003/0045437 A1 | 3/2003 | Ward |
| 2004/0259748 A1 | 12/2004 | Wiedemann et al. |
| 2004/0259749 A1 | 12/2004 | Braeckman et al. |
| 2005/0164897 A1 | 7/2005 | Speed et al. |
| 2005/0202995 A1 | 9/2005 | Waits et al. |
| 2006/0069001 A1 | 3/2006 | Song |
| 2006/0216424 A1 | 9/2006 | Maurer et al. |
| 2007/0203047 A1 | 8/2007 | Pegelow et al. |
| 2008/0063774 A1 | 3/2008 | Aehle et al. |
| 2008/0193999 A1 | 8/2008 | Andersen et al. |
| 2008/0293604 A1 | 11/2008 | Gibis et al. |
| 2008/0293610 A1 | 11/2008 | Shaw et al. |
| 2009/0183755 A1 | 7/2009 | Jekel et al. |
| 2009/0233831 A1 | 9/2009 | Souter |
| 2009/0275078 A1 | 11/2009 | Andersen et al. |
| 2009/0325840 A1 | 12/2009 | Preuschen |
| 2010/0075884 A1 | 3/2010 | Brooker |
| 2010/0152088 A1 | 6/2010 | Estell et al. |
| 2010/0170302 A1 | 7/2010 | Housmekerides et al. |
| 2010/0190676 A1 | 7/2010 | Smith et al. |
| 2011/0081454 A1 | 4/2011 | Hommes et al. |
| 2011/0212876 A1 | 9/2011 | Meek et al. |
| 2011/0268778 A1 | 11/2011 | Dihora |
| 2011/0284032 A1 | 11/2011 | Souter |
| 2012/0053103 A1 | 3/2012 | Sivik et al. |
| 2012/0067373 A1 | 3/2012 | Souter et al. |
| 2012/0291815 A1 | 11/2012 | Monsrud et al. |
| 2013/0000055 A1 | 1/2013 | Jackson et al. |
| 2013/0025073 A1 | 1/2013 | Souter et al. |
| 2013/0045910 A1 | 2/2013 | Miracle et al. |
| 2013/0072415 A1 | 3/2013 | Scheibel et al. |
| 2013/0157345 A1 | 6/2013 | Smith et al. |
| 2013/0203644 A1 | 8/2013 | Lant et al. |
| 2013/0206181 A1 | 8/2013 | Giles et al. |
| 2013/0217607 A1 | 8/2013 | Souter et al. |
| 2014/0005094 A1 * | 1/2014 | Aehle .................. C11D 3/386 510/374 |
| 2014/0024103 A1 | 1/2014 | Benie et al. |
| 2014/0038876 A1 | 2/2014 | Ostergaard et al. |
| 2014/0106439 A1 | 4/2014 | Mussmann et al. |
| 2014/0134709 A1 * | 5/2014 | Andersen .......... C11D 3/38609 435/264 |
| 2014/0141489 A1 | 5/2014 | Kaasgaard et al. |
| 2014/0206026 A1 | 7/2014 | Kaasgaard et al. |
| 2014/0251385 A1 | 9/2014 | Kelly-Murray et al. |
| 2014/0315775 A1 | 10/2014 | Hommes et al. |
| 2014/0357541 A1 | 12/2014 | Miracle et al. |
| 2015/0057212 A1 | 2/2015 | Hulskotter et al. |
| 2015/0057213 A1 | 2/2015 | Hulskotter et al. |
| 2015/0239798 A1 | 8/2015 | Scheibel et al. |
| 2015/0240190 A1 | 8/2015 | Sakurai et al. |
| 2015/0291917 A1 | 10/2015 | Eiting et al. |
| 2016/0177229 A1 | 6/2016 | Souter et al. |
| 2016/0177230 A1 | 6/2016 | Souter et al. |
| 2016/0177231 A1 | 6/2016 | Souter et al. |
| 2016/0177232 A1 | 6/2016 | Souter et al. |
| 2016/0177235 A1 | 6/2016 | Brooker et al. |
| 2016/0177236 A1 | 6/2016 | Brooker et al. |

FOREIGN PATENT DOCUMENTS

| | | |
|---|---|---|
| EP | 2361964 A1 | 8/2011 |
| JP | 06121760 A | 5/1994 |
| JP | 2005-154716 A | 6/2005 |
| JP | 2012-1663 A | 1/2012 |
| JP | 2013-192526 A | 9/2013 |
| JP | 2014-534990 A | 12/2014 |
| WO | WO 91/08281 A1 | 6/1991 |
| WO | WO9206159 A1 | 4/1992 |
| WO | WO 94/02597 A1 | 2/1994 |
| WO | WO 94/18314 A1 | 8/1994 |
| WO | WO 95/10603 A1 | 4/1995 |
| WO | WO 96/23873 A1 | 8/1996 |
| WO | WO 98/14547 A2 | 4/1998 |
| WO | WO9910466 A1 | 3/1999 |
| WO | WO 99/019467 A1 | 4/1999 |
| WO | WO 99/23211 A1 | 5/1999 |
| WO | WO0004129 A2 | 1/2000 |
| WO | WO 00/60060 A2 | 10/2000 |
| WO | WO 02/10355 A2 | 2/2002 |
| WO | WO2003/042347 A1 | 5/2003 |
| WO | WO2003/090576 A2 | 7/2003 |
| WO | WO 2007/044993 A2 | 4/2007 |
| WO | WO 2007/083141 A1 | 7/2007 |
| WO | WO2009112992 A1 | 9/2009 |
| WO | WO2010/079467 A2 | 7/2010 |
| WO | WO2010/079468 A2 | 7/2010 |
| WO | WO2010/084480 A2 | 7/2010 |
| WO | WO 2011/098531 A1 | 8/2011 |
| WO | WO 2014/071410 A1 | 5/2014 |
| WO | WO 2014/194032 A1 | 12/2014 |
| WO | WO 2014/194034 A2 | 12/2014 |
| WO | WO 2014/194054 A1 | 12/2014 |

OTHER PUBLICATIONS

U.S. Appl. No. 14/961,935, filed Dec. 8, 2015, Souter et al.
EP Search Report; dated Jun. 17, 2015; 6 Pages.
EP Search Report; dated Jun. 17, 2015; 10 Pages.
EP Search Report; dated Mar. 26, 2015; 8 Pages.
EP Search Report; dated Jun. 1, 2015; 6 Pages.
EP Search Report; dated Jun. 2, 2015; 6 Pages.
Product in formation Protease Enzymes/Neutrase; Retrieved May 16, 2017 from http://www.novozymes.com/en/solutions/pharmaceuticals/biocatalysis/protease-enzymes.
Sigma Product Information, P1512; Retrieved from < http://www.sigmaaldrich.com/catalog/search?term=lyophilized+thermolysin&interface=All&N=0&mode=match%20partialmax&lang=en&region=US&focus=product> and < http://www.sigmaaldrich.com/catalog/product/sigma/p1512?lang=en&region=US > on Sep. 19, 2017.
UniProt accession Q59223, Retrieved from < http://www.uniprot.org/uniprot/Q59223 > on Sep. 20, 2017.
Kubo, et al., "Cloning and Nucleotide Sequence of the Highly Thermostable Neutral Protease Gene from Bacillus Stearothermophilus", J. General Microbiology, 1988, 134: 1883-1892.

* cited by examiner

SEQUENCE LISTING

<160> NUMBER OF SEQ ID NOS: 6

<210> SEQ ID NO 1
<211> LENGTH: 316
<212> TYPE: PRT
<213> ORGANISM: Bacillus thermoproteolyticus

<400> SEQUENCE: 1

```
Ile Thr Gly Thr Ser Thr Val Gly Val Gly Arg Gly Val Leu Gly Asp
1               5                   10                  15

Gln Lys Asn Ile Asn Thr Thr Tyr Ser Thr Tyr Tyr Tyr Leu Gln Asp
            20                  25                  30

Asn Thr Arg Gly Asn Gly Ile Phe Thr Tyr Asp Ala Lys Tyr Arg Thr
        35                  40                  45

Thr Leu Pro Gly Ser Leu Trp Ala Asp Ala Asp Asn Gln Phe Phe Ala
    50                  55                  60

Ser Tyr Asp Ala Pro Ala Val Asp Ala His Tyr Tyr Ala Gly Val Thr
65                  70                  75                  80

Tyr Asp Tyr Tyr Lys Asn Val His Asn Arg Leu Ser Tyr Asp Gly Asn
                85                  90                  95
```

-continued

```
Asn Ala Ala Ile Arg Ser Ser Val His Tyr Ser Gln Gly Tyr Asn Asn
                100                 105                 110

Ala Phe Trp Asn Gly Ser Gln Met Val Tyr Gly Asp Gly Asp Gly Gln
            115                 120                 125

Thr Phe Ile Pro Leu Ser Gly Gly Ile Asp Val Val Ala His Glu Leu
        130                 135                 140

Thr His Ala Val Thr Asp Tyr Thr Ala Gly Leu Ile Tyr Gln Asn Glu
145                 150                 155                 160

Ser Gly Ala Ile Asn Glu Ala Ile Ser Asp Ile Phe Gly Thr Leu Val
                165                 170                 175

Glu Phe Tyr Ala Asn Lys Asn Pro Asp Trp Glu Ile Gly Glu Asp Val
            180                 185                 190

Tyr Thr Pro Gly Ile Ser Gly Asp Ser Leu Arg Ser Met Ser Asp Pro
        195                 200                 205

Ala Lys Tyr Gly Asp Pro Asp His Tyr Ser Lys Arg Tyr Thr Gly Thr
    210                 215                 220

Gln Asp Asn Gly Gly Val His Ile Asn Ser Gly Ile Ile Asn Lys Ala
225                 230                 235                 240

Ala Tyr Leu Ile Ser Gln Gly Gly Thr His Tyr Gly Val Ser Val Val
                245                 250                 255

Gly Ile Gly Arg Asp Lys Leu Gly Lys Ile Phe Tyr Arg Ala Leu Thr
            260                 265                 270

Gln Tyr Leu Thr Pro Thr Ser Asn Phe Ser Gln Leu Arg Ala Ala Ala
        275                 280                 285

Val Gln Ser Ala Thr Asp Leu Tyr Gly Ser Thr Ser Gln Glu Val Ala
    290                 295                 300

Ser Val Lys Gln Ala Phe Asp Ala Val Gly Val Lys
305                 310                 315

<210> SEQ ID NO 2
<211> LENGTH: 300
<212> TYPE: PRT
<213> ORGANISM: Bacillus amyloliquefaciens

<400> SEQUENCE: 2

Ala Ala Thr Thr Gly Thr Gly Thr Leu Lys Gly Lys Thr Val Ser
1               5                   10                  15

Leu Asn Ile Ser Ser Glu Ser Gly Lys Tyr Val Leu Arg Asp Leu Ser
                20                  25                  30

Lys Pro Thr Gly Thr Gln Ile Ile Thr Tyr Asp Leu Gln Asn Arg Glu
            35                  40                  45

Tyr Asn Leu Pro Gly Thr Leu Val Ser Ser Thr Thr Asn Gln Phe Thr
        50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160
```

```
Gln Pro Gly Ala Leu Asn Glu Ser Phe Ser Asp Val Phe Gly Tyr Phe
            165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
            195                 200                 205

Asn Phe Lys Asn Tyr Lys Asn Leu Pro Asn Thr Asp Ala Gly Asp Tyr
            210                 215                 220

Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
            245                 250                 255

Ala Leu Thr Val Tyr Leu Thr Pro Ser Ser Thr Phe Lys Asp Ala Lys
            260                 265                 270

Ala Ala Leu Ile Gln Ser Ala Arg Asp Leu Tyr Gly Ser Gln Asp Ala
            275                 280                 285

Ala Ser Val Glu Ala Ala Trp Asn Ala Val Gly Leu
            290                 295                 300

<210> SEQ ID NO 3
<211> LENGTH: 483
<212> TYPE: PRT
<213> ORGANISM: Bacillus licheniformis

<400> SEQUENCE: 3

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
            85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
            115                 120                 125

Ile Ser Gly Glu His Arg Ile Lys Ala Trp Thr His Phe His Phe Pro
        130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
            165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
            195                 200                 205

Ala Ala Glu Ile Lys Arg Trp Gly Thr Trp Tyr Ala Asn Glu Leu Gln
            210                 215                 220

Leu Asp Gly Phe Arg Leu Asp Ala Val Lys His Ile Lys Phe Ser Phe
```

```
                225                 230                 235                 240
Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Tyr Asp Met
        290                 295                 300

Arg Lys Leu Leu Asn Ser Thr Val Val Ser Lys His Pro Leu Lys Ala
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
        370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
                450                 455                 460

Glu Gly Trp Gly Glu Phe His Val Asn Gly Gly Ser Val Ser Ile Tyr
465                 470                 475                 480

Val Gln Arg

<210> SEQ ID NO 4
<211> LENGTH: 485
<212> TYPE: PRT
<213> ORGANISM: Bacillus AA560

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
```

```
            115                 120                 125
Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 5
<211> LENGTH: 485
<212> TYPE: PRT
<213> ORGANISM: Bacillus sp722

<400> SEQUENCE: 5
```

```
His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
    195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
    275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
            325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
    355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
            405                 410                 415

Gly Asn Thr Thr His Pro Asn Ser Gly Leu Ala Thr Ile Met Ser Asp
```

```
                420             425             430
Gly Pro Gly Gly Glu Lys Trp Met Tyr Val Gly Gln Asn Lys Ala Gly
            435             440             445

Gln Val Trp His Asp Ile Thr Gly Asn Lys Pro Gly Thr Val Thr Ile
    450             455             460

Asn Ala Asp Gly Trp Ala Asn Phe Ser Val Asn Gly Ser Val Ser
465             470             475             480

Ile Trp Val Lys Arg
            485

<210> SEQ ID NO 6
<211> LENGTH: 485
<212> TYPE: PRT
<213> ORGANISM: Bacillus sp. 707

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65              70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145             150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225             230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300
```

```
Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
            485
```

DETERGENT COMPOSITION

TECHNICAL FIELD

The present invention is in the field of cleaning. It relates to a cleaning product, in particular a low pH automatic dishwashing detergent composition comprising an amylase and a lime soap dispersing agent.

BACKGROUND OF THE INVENTION

The automatic dishwashing detergent formulator is continuously looking for ways to improve the performance of detergents. Items placed in a dishwasher to be washed tend to be soiled with a plurality of different soils. Starchy soils are particularly difficult to remove. Starch can be strongly attached to the soiled substrates. Usually the removal of starchy soils takes longer that the detachment of other soils from the substrates. Sometimes other soils present in the wash liquor end up depositing over starchy soils thereby reducing the access of cleaning actives to them thereby impairing their removal. The removal of starchy soils in automatic dishwashing can be challenging and this may not only impact the cleaning but also the finishing of the cleaned items. Starchy residues can be left on the washed items and they can contribute to the formation of streaks, filming and spotting.

The automatic dishwashing detergent formulator is not only looking for a detergent composition that provides good cleaning but it also looks for a composition that at the same time provides a good finishing, i.e., leave the washed items free of streaks, filming and spotting. In addition, the composition should be environmentally friendly, provide care for the washed items and works in low-energy consumption programs, such as low temperature and short cycles.

The objective of the present invention is to provide an automatic dishwashing composition capable of providing good cleaning and finishing of the washed items. Preferably, the composition should be environmentally friendly and work in low-energy consumption programs.

SUMMARY OF THE INVENTION

According to a first aspect of the invention, there is provided a low pH automatic dishwashing detergent composition.

The composition of the invention has a "low pH", by a low pH composition is herein meant a composition having a pH of from about 5 to about 7.5 as measured in 1% weight aqueous solution (distilled water) at 25° C. In addition to good cleaning and shine, this pH is quite gentle on the washed items, it is not as aggressive as commonly used alkaline compositions and therefore keep washed items such as glasses, patterned ware, etc looking new for longer.

Preferably, the composition of the invention has a pH of from about 5 to about 6.9 as measured in 1% weight aqueous solution (distilled water) at 25° C. This pH provides even better cleaning and shine. This pH seems to be good for cleaning and finishing.

The composition of the invention comprises an amylase and a lime soap dispersing agent, the lime soap dispersing agent preferably also provides swelling of the soil, in particular greasy soils. It seems that the amylase and the lime soap dispersant agent work in synergy to provide very good cleaning and shine. Without being bound by theory it is believed that the lime soap dispersing agent keeps the soil, especially greasy soils, suspended leaving the starchy part of soils exposed this facilitate the access of the amylase of the invention to the starch. Preferred lime soap dispersing agents for use herein are surfactants, preferably anionic surfactants, especially an alkyl ethoxy sulfate and/or performance polymers, preferably dispersant polymer especially an alkoxylated polyalkyleneimine Preferably, the amylase of the composition of the invention is a low temperature amylase.

Preferably, the composition of the invention is "substantially builder-free".

For the purpose of this invention a "substantially builder-free composition" is a composition comprising less than 10%, preferably less than 5%, more preferably less than 1% and especially less than 0.1% by weight of the composition of builder. Builders are cleaning actives widely used in automatic dishwashing detergents, in particular in alkaline compositions. Most, if not all, of the automatic dishwashing detergents available in the market are alkaline and comprise builders. Compounds that would act as builder under alkaline conditions would probably not be good builders under the low pH conditions of the composition of the invention. Builders can sequester calcium and other ions, from soils and from water greatly contributing to cleaning. The downside of using builders is that they can precipitate and give rise to filming and spotting on the washed items. The formulation approach used in the composition of the present invention overcomes the filming and spotting issues. The washed items, in particular, glass items are left clear and shiny.

The soils brought into the wash liquor during the automatic dishwashing process can greatly alter the pH of the wash liquor. In order to provide optimum cleaning the pH of the wash liquor should not vary too much. This is achieved with the composition of the present invention by the presence of a buffer that helps to keep the pH of the wash liquor within a desired range.

The composition of the invention comprises a buffer. By "buffer" is herein meant an agent that when present in a wash liquor is capable of maintaining the pH of the liquor within a narrow range. By a "narrow range" is herein meant that the pH changes by less than 2 pH units, more preferably by less than 1 pH unit.

Preferably the buffer comprises an organic acid, preferably a carboxylic acid and more preferably the buffer is selected from a polycarboxylic acid, its salt and mixtures thereof.

The composition of the invention can optionally comprise an iron chelant. These compositions provide good cleaning of bleachable stains, even in the absence of bleach. Without being bound by theory, it is believed that the iron chelant removes the heavy metals that form part of bleachable stains, thereby contributing to the loosening of the stain. The stain tends to detach itself from the ware. The cleaning can be further helped by the lime soap dispersing polymer that would help with the suspension of the stain. Under the low pH conditions provided by the compositions of the invention, when the heavy metals are taken from the bleachable stain, the stain becomes particulate and the lime soap dispersing agent help with suspension. Preferred iron chelants for use herein have been found to be 1,2-dihydroxybenzene-3,5-disulfonic acid, hydroxypyridine N-Oxides, in particular hydroxypyridine N-Oxides and mixtures thereof.

It has also been found that small levels of bleach in the composition of the invention provide a level of bleaching much greater than expected. It has also been found that the bleaching occurs faster and at lower temperatures than using conventional alkaline detergents.

Without being bound by theory, it is believed that the iron ions present into the wash liquor (brought by soils, such as tea, beef, etc, impurities in detergent components and/or water) act as catalyst for the bleach to generate bleaching radicals. This effect is most pronounced when an iron chelant is used and it is believed this is because the iron chelant binds the iron to generate metal catalysts in situ that when combined with the bleach are able to drive excellent bleach cleaning.

The cleaning provided by the compositions of the invention is further improved when the composition comprises a crystal growth inhibitor, in particular HEDP.

The performance provided by the compositions of the invention is further improved by anionic surfactant, when the composition comprises anionic surfactant, the use of a suds suppressor is preferred. Anionic surfactants can generate suds during the automatic dishwashing process however the suds generation with the composition of the invention is less that the suds generation under alkaline conditions, thus the level of suds suppressor required is lower than what it would be for an alkaline composition.

Preferred compositions further comprise proteases. In particular proteases selected from the group consisting of:
 (i) a metalloprotease;
 (ii) a cysteine protease;
 (iii) a neutral serine protease;
 (iv) an aspartate protease, and
 (v) mixtures thereof.

These proteases perform well in the low pH composition of the invention. Some of the proteases present in conventional alkaline detergents do not perform well at the pH of the composition of the invention. Also preferred are endoproteases, preferably those with an isoelectric point of from about 4 to about 9 and more preferably from about 4.5 to about 6.5. Compositions comprising proteases having these isoelectric points perform very well in the low pH compositions of the invention.

The compositions of the invention are very suitable to be packed in unit-dose form. The compositions are so effective that only a low level needs to be used in the dishwasher to provide outstanding results thereby allowing for very compact packs. The pack of the invention, preferably in the form of a pouch has a weight of from about 5 to about 40 grams, more preferably from about 5 to about 25 grams, more preferably from about 7 to about 20 grams and especially from about 7 to about 15 grams. The pack of the invention comprises a water-soluble material enveloping the composition of the invention, preferably a polyvinyl alcohol film. The packs can have a single compartment or a plurality of compartments.

According to a second aspect of the invention, there is provided a method of automatic dishwashing comprising the step of subjecting the ware to a wash liquor comprising the composition of the invention.

The elements of the composition of the invention described in connection with the first aspect of the invention apply mutatis mutandis to the second aspect of the invention.

SUMMARY OF THE INVENTION

The present invention encompasses an automatic dishwashing detergent composition. The composition has a low pH, comprises an amylase and a lime soap dispersing agent. The composition provides excellent cleaning, finishing, care and performs very well in short and/or low temperature cycles. The invention also encompasses a method of automatic dishwashing using the composition of the invention.

Detergent Composition

The detergent composition of the invention can be in any physical form including solid, liquid and gel form. The composition of the invention is very well suited to be presented in unit-dose form, in particular in the form of a multi-compartment pack, more in particular a multi-compartment pack comprising compartments with compositions in different physical forms, for example a compartment comprising a composition in solid form and another compartment comprising a composition in liquid form. Due to the efficacy of the composition, the packs can be compact.

The composition of the invention has a pH as measured in 1% weight aqueous solution at 25° C. of from about 5 to about 7.5, preferably from about 5 to less than about 6.9 and more preferably from about 5 to about 6.5.

Enzyme-Related Terminology

Nomenclature for Amino Acid Modifications

In describing enzyme variants herein, the following nomenclature is used for ease of reference: Original amino acid(s):position(s):substituted amino acid(s).

According to this nomenclature, for instance the substitution of glutamic acid for glycine in position 195 is shown as G195E. A deletion of glycine in the same position is shown as G195*, and insertion of an additional amino acid residue such as lysine is shown as G195GK. Where a specific enzyme contains a "deletion" in comparison with other enzyme and an insertion is made in such a position this is indicated as *36D for insertion of an aspartic acid in position 36. Multiple mutations are separated by pluses, i.e.: S99G+V102N, representing mutations in positions 99 and 102 substituting serine and valine for glycine and asparagine, respectively. Where the amino acid in a position (e.g. 102) may be substituted by another amino acid selected from a group of amino acids, e.g. the group consisting of N and I, this will be indicated by V102N/I.

In all cases, the accepted IUPAC single letter or triple letter amino acid abbreviation is employed.

Where multiple mutations are employed they are shown with either using a "+" or a "/", so for instance either S126C+P127R+S128D or S126C/P127R/S128D would indicate the specific mutations shown are present in each of positions 126, 127 and 128.

Amino Acid Identity

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of an enzyme used herein ("invention sequence") and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity. An exact match occurs when the "invention sequence" and the "foreign sequence" have identical amino acid residues in the same positions of the overlap. The length of a sequence is the number of amino acid residues in the sequence.

Amylase

The amylase of the composition of the invention is a low temperature amylases. Compositions comprising low temperature amylases allow for a more energy efficient dishwashing processes without compromising in cleaning.

As used herein, "low temperature amylase" is an amylase that demonstrates at least 1.2, preferably at least 1.5 and more preferably at least 2 times the relative activity of the reference amylase at 25° C. As used herein, the "reference amylase" is the amylase of SEQ ID NO:3, commercially available under the tradename of Termamyl™ (Novozymes A/S). As used herein, "relative activity" is the fraction derived from dividing the activity of the enzyme at the temperature assayed versus its activity at its optimal temperature measured at a pH of 9.

Amylases for use herein can be derived from bacteria, fungi or plants. Suitable amylases (α and/or β) include those of bacterial or fungal origin. Chemically modified or protein engineered mutants are included. Amylases include, for example, α-amylases obtained from *Bacillus*. Amylases of this invention preferably display some α-amylase activity. Preferably said amylases belong to EC Class 3.2.1.1.

Amylases for use herein, including chemically or genetically modified mutants (variants), are amylases possessing at least 80%, or 85%, or 90%, preferably 95%, more preferably 98%, even more preferably 99% and especially 100% identity, with those derived from *Bacillus Licheniformis, Bacillus amyloliquefaciens, Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334).

Preferred amylases include:

(a) the variants of a parent amylase, said parent amylase having at least 60%, preferably 80%, more preferably 85%, more preferably 90%, more preferably 95%, more preferably 96%, more preferably 97%, more preferably 98%, more preferably 99% and specially 100% identity to SEQ ID NO:4. The variant amylase preferably further comprises one or more substitutions in the following positions versus SEQ ID NO: 4 of this patent:

9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482, 484 and preferably the variant amylase comprises the deletions of D183* and G184*.

Preferred amylases include those comprising substitutions at one or more of the following positions versus SEQ ID NO:4:

i) one or more, preferably two or more, more preferably three or more substitutions in the following positions versus SEQ ID NO: 4: 9, 26, 149, 182, 186, 202, 257, 295, 299, 323, 339 and 345; and optionally with one or more, preferably four or more of the substitutions and/or deletions in the following positions: 118, 183, 184, 195, 320 and 458, which if present preferably comprise R118K, D183*, G184*, N195F, R320K and/or R458K.

Preferred amylases include variants of a parent amylase, said parent amylase having at least 60%, or 80%, or 85% or 90% or 95% or 96% or 97% or 98% or 99% or even 100% identity to SEQ ID NO:4, comprising the following sets of mutations versus SEQ ID NO:4:

(i) M9L+, M323T;
(ii) M9L+M202L/T/V/I+M323T;
(iii) M9L+N195F+M202L/T/V/I+M323T;
(iv) M9L+R118K+D183*+G184*+R320K+M323T+R458K;
(v) M9L+R118K+D183*+G184*+M202L/T/V/I; R320K+M323T+R458K;
(vi) M9L+G149A+G182T+G186A+M202L+T257I+Y295F+N299Y+M323T+A339S+E345R;
(vii) M9L+G149A+G182T+G186A+M202I+T257I+Y295F+N299Y+M323T+A339S+E345R;
(viii) M9L+R118K+G149A+G182T+D183*+G184*+G186A+M202L+T257I+Y295F+N299Y+R320K+M323T+A339S+E345R+R458K;
(ix) M9L+R118K+G149A+G182T+D183*+G184*+G186A+M202I+T257I+Y295F+N299Y+R320K+M323T+A339S+E345R+R458K;
(x) M9L+R118K+D183*+D184*+N195F+M202L+R320K+M323T+R458K;
(xi) M9L+R118K+D183*+D184*+N195F+M202T+R320K+M323T+R458K;
(xii) M9L+R118K+D183*+D184*+N195F+M202I+R320K+M323T+R458K;
(xiii) M9L+R118K+D183*+D184*+N195F+M202V+R320K+M323T+R458K;
(xiv) M9L+R118K+N150H+D183*+D184*+N195F+M202L+V214T+R320K+M323T+R458K; or
(xv) M9L+R118K+D183*+D184*+N195F+M202L+V214T+R320K+M323T+E345N+R458K.

Suitable amylases for use herein include those described in U.S. Pat. No. 5,856,164 and WO99/23211, WO 96/23873, WO00/60060 and WO 06/002643.

b) variants exhibiting at least 90% identity with SEQ ID NO:5, especially variants comprising deletions in the 183 and 184 positions and/or substitutions at one or more of the following positions 93, 116, 118, 129, 133, 134, 140, 142, 146, 147, 149, 151, 152, 169, 174, 186, 189, 193, 195, 197, 198, 200, 203, 206, 210, 212, 213, 235, 243, 244, 260, 262, 284, 303, 304, 320, 338, 347, 359, 418, 431, 434, 439, 447, 458, 469, 476 and 477, Preferred substitutions include E260A/D/C/Q/L/M/F/P/S/W/V/G/H/I/K/N/R/T/Y, G304R/K/E/Q, W140Y/F, W189E/G/T, D134E, F262G/P, W284D/H/F/Y/R, W347H/F/Y, W439R/G, G476E/Q/R/K, G477E/Q/K/M/R, N195F/Y, N197F/L, Y198N, Y200F, Y203F, I206H/L/N/F/Y, H210Y, E212V/G, V213A, M116T, Q129L, G133E, E134Y, K142R, P146S, G147E, G149R, N151R, Y152H, Q169E, N174R, A186R, Y243F, S244Q, G303V, R320N, R359I, N418D and A447V.

Also preferred are and variants described in WO00/60060, WO2011/100410 and WO2013/003659.

(c) variants exhibiting at least having at least 60%, preferably 80%, more preferably 85%, more preferably 90%, more preferably 95%, more preferably 96%, more preferably 97%, more preferably 98%, more preferably 99% and specially 100% identity to SEQ ID NO:6, the wild-type enzyme from *Bacillus* sp. 707, especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

Other suitable amylases for use herein include amylases from *Bacillus stearothermophilus*, having SEQ ID NO: 6 in WO 02/010355 or variants thereof having 90% sequence identity. Preferred variants of *Bacillus stearothermophilus* are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 of WO 2006/066594 are those having the substitutions:

M197T;
H156Y+A181T+N190F+A209V+Q264S; or
G48A+T49I+G107A+H156Y+A181T+N190F+I201 F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269.

Particularly preferred amylases are those having deletion in positions R181 and G182, or positions H183 and G184.

Additional amylases which can be used are those having SEQ ID NO: 1 of WO 96/023873, SEQ ID NO: 3 of WO 96/023873, SEQ ID NO: 2 of WO 96/023873 or SEQ ID NO: 7 of WO 96/023873 or variants thereof having 90% sequence identity to SEQ ID NO: 1, SEQ ID NO: 2, SEQ ID NO: 3 or SEQ ID NO: 7 of WO 96/023873. Preferred variants of SEQ ID NO: 1 of WO 96/023873, SEQ ID NO: 3 of WO 96/023873, SEQ ID NO: 2 of WO 96/023873 or SEQ ID NO: 7 of WO 96/023873 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1 of WO 96/023873, SEQ ID NO: 2 of WO 96/023873 or SEQ ID NO: 7 of WO 96/023873 are those having a deletion in positions 183 and 184 and a substitution in one or more of positions 140, 195, 206, 243, 260, 304 and 476.

Other amylases which can be used are amylases having SEQ ID NO: 2 of WO08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E/R, Q98R, S125A, N128C, T131 I, T165I, K178L, T182G, M201L, F202Y, N225E/R, N272E/R, S243Q/A/E/D, Y305R, R309A, Q320R, Q359E, K444E and G475K and/or deletion in position R180 and/or S181 or of T182 and/or G183. Most preferred amylase variants of SEQ ID NO: 2 are those having the substitutions: N128C+K178L+T182G+Y305R+G475K; N 128C+K178L+T182G+F202Y+Y305R+D319T+G475K; S125A+N128C+K178L+T182G+Y305R+G475K; or S125A+N128C+T131 I+T165I+K178L+T182G+Y305R+ G475K wherein the variants are C-terminally truncated and optionally further comprises a substitution at position 243 and/or a deletion at position 180 and/or position 181.

Other examples are amylase variants such as those described in WO2011/098531, WO2013/001078 and WO2013/001087.

Preferred commercially available amylases for use herein are STAINZYME®, STAINZYME PLUS®, STAINZYME ULTRA®, EVEREST® and NATALASE® (Novozymes A/S) and RAPIDASE, POWERASE® and the PREFERENZ S® series, including PREFERENZ 5100® (DuPont).

Examples of other amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Examples of such commercially available amylases are TERMAMYL ULTRA® and DURAMYL®.

If the amylase is derived from the wild-types of *Bacillus Licheniformis* or *Bacillus Amyloliquefaciens*, it is an engineered variant thereof comprising at least one mutation designed to impart performance optionally with superior stability. The amylase is preferably not BAN®.

The composition of the invention preferably comprises from 0.001 to 2%, more preferably from 0.003 to 1%, more preferably from 0.007 to 0.3% and especially from 0.01 to 0.1% by weight of the composition of active amylase.

Lime Soap Dispersing Agent

The composition of the invention comprises a lime soap dispersing agent, which has a lime soap dispersing power (LSDP), as defined hereinafter of no more than 25, preferably no more than 12, most preferably no more than 8. The lime soap dispersing is present at a level of from 0.1% to 40% by weight, more preferably 1% to 20% by weight, most preferably from 2% to 10% by weight of the compositions.

A lime soap dispersing agent is a material that prevents the precipitation of alkali metal, ammonium or amine salts of fatty acids by calcium or magnesium ions. A numerical measure of the effectiveness of a lime soap dispersing agent is given by the lime soap dispersing power (LSDP) which is determined using the lime soap dispersion test as described in an article by H. C. Borghetty and CA. Bergman, *J. Am. Oil. Chem. Soc*, volume 27, pages 88-90, (1950). This lime soap dispersion test method is widely used by practitioners in this art field being referred to, for example, in the following review articles; W. N. Linfield, Surfactant Science Series, Volume 7, p 3; W. N. Linfield, Tenside Surf. Det., Volume 27, pages 159-161, (1990); and M. K. Nagarajan, W. F. Masler, Cosmetics and Toiletries, Volume 104, pages 71-73, (1989). The LSDP is the % weight ratio of dispersing agent to sodium oleate required to disperse the lime soap deposits formed by 0.025 g of sodium oleate in 30 ml of water of 333 ppmCaCO$_3$ (Ca:Mg=3:2) equivalent hardness.

In the Borghetty/Bergman lime soap dispersion test 5 ml of a 0.5% by weight solution of sodium oleate is added to a test tube, followed by 10 ml of a hard water solution containing 600 ppm $Ca^{2+}$ and 400 ppm $Mg^{2+}$ (1000 ppm as $CaCO_3$ equivalent, 70° Clark Hardness) which will cause formation of a lime soap deposit (or curd). An arbitrary amount (less than 15 ml) of dispersing agent as a 0.25% by weight solution is then added to the test tube. The total volume of solution in the test tube is then made up to 30 ml and the test tube is stoppered, inverted 20 times and then allowed to stand for 30 seconds. The contents of the test tube are then visually inspected to check if the lime soap deposits are still intact or whether they have been dispersed into the solution. The test procedure is repeated using different amounts of dispersing agent solution until the minimum amount of dispersing agent solution which will cause dispersion of the lime soap deposits is obtained.

The lime soap dispersing power is then obtained as:

LSDP=(weight of lime soap dispersing agent)×100/(weight of sodium oleate).

Thus in accord with the test method described above a material with a lower LSDP is a more weight effective lime soap dispersant than one with a higher LSDP.

A listing of suitable lime soap dispersants for use in accord with the invention is given in the above mentioned review by M. Linfield to be found in Tenside. Sust. Det., Volume 27, pages 159-161 (1990).

Polymeric lime soap dispersing agents suitable for use herein are described in the above mentioned article by M. K. Nagarajan and W. F. Masler, to be found in Cosmetics and Toiletries, Volume 104, pages 71-73, (1989). Examples of such polymeric lime soap dispersing agents and include certain water-soluble salts of copolymers of acrylic acid, methacrylic acid or mixtures thereof, and an acrylamide or substituted acrylamide, where such polymers typically have a molecular weight of from 5,000 to 20,000.

Surfactants having good lime soap dispersant capability will include certain amine oxides, betaines, sulfobetaines, alkyl ethoxysulfates and ethoxylated alcohols. Specially preferred lime soap dispersing agents are alkyl ethoxysulfates.

Exemplary surfactants having a LSDP of no more than 8 for use in accord with the invention include C16-C18 dimethyl amine oxide, C12-C18 alkyl ethoxysulfates with an average degree of ethoxylation of from 1-5, particularly C12-C15 alkyl ethoxysulfate surfactant with a degree of ethoxylation of about 3 (LSDP of about 4), and the C13-C15 ethoxylated alcohols with an average degree of ethoxylation of either 12 (LSDP of about 6) or 30, sold under the trade names Lutensol A012 and Lutensol A030 respectively, by BASF GmbH.

Preferably the lime soap dispersing agent can act as a soil swelling agent. A soil swelling agent is a substance or composition effective in swelling a soil.

The soil swelling index (SSI) is a measure of the increased thickness of soil after treatment with a substance or composition in comparison to the soil before treatment with the substance or composition. Swelling of the soil makes the soil easier to remove with no or minimal application of force. The measuring of this change of soil thickness gives the SSI. The amount of substance or composition necessary to provide soil swelling functionality will depend upon the nature of the substance or composition and can be determined by routine experimentation. Other conditions effective for soil swelling such as pH, temperature and treatment time can also be determined by routine experimentation. Preferred herein, however are substances and compositions effective in swelling soils such as polymerized grease or carbohydrate soils or proteinaceous soils on glass or metal substrates, whereby after the substance or composition has been in contact with the soil for 45 minutes or less, preferably 30 min or less and more preferably 20 min or less at 20° C., the substance or composition has an SS1 at 5% in an aqueous solution and pH of 9 of at least about 15%, preferably at least about 20% more preferably at least about 30% and especially at least about 50%. Preferably also the choice of soil swelling agent is such that the final compositions have an SS1 measured as neat liquids under the same treatment time and temperature conditions of at least about 100%, preferably at least about 200% and more preferably at least about 500%. Highly preferred soil swelling agents and final compositions herein meet the SSI requirements on polymerized grease soils according to the procedure set out below.

SS1 is determined herein by optical profilometry, using, for example, a Zygo NewView 5030 Scanning white Light Interferometer®. A sample of polymerized grease on a brushed, stainless steel coupon is prepared as described herein below with regard to the measurement of polymerized grease removal index. Optical profilometry is then run n a small droplet of approximately 10 □m thickness of the grease at the edge of the grease sample. The thickness of the soil droplet before (Si) and after (Sf) treatment is measured by image acquisition by means of scanning white light interferometry. The interferometer (Zygo NewView 5030® with 20× Mirau objective) splits incoming light into a beam that goes to an internal reference surface and a beam that goes to the sample. After reflection, the beams recombine inside the interferometer, undergo constructive and destructive interference, and produce a light and dark fringe pattern. The data are recorded using a CCD (charged coupled device) camera and processed by the software of the interferometer using Frequency Domain Analysis. The dimension of the image obtained (in pixels) is then converted in real dimension (pm or mm). After the thickness of the soil $(S_i)$ on the coupon has been measured the coupon is soaked in the invention composition at ambient temperature for a given length of time and the thickness of the soil $(S_f)$ is measured repeating the procedure set out above. If necessary, the procedure is replicated over a sufficient member of droplets and samples to provide statistical significance.

The SS1 is calculated in the following manner:

$$SSI=[(S_f-S_i)/S_i]\times 100$$

Preferred lime soap dispersing agents for use herein are selected from performance polymers, anionic surfactants and mixtures thereof Performance Polymer Preferably the composition of the invention comprises from 0.1% to about 5%, preferably from about 0.2% to about 3% by weight of the composition of a performance polymer. Suitable polymers include alkoxylated polyalkyleneimines, polymeric polycarboxylates, including alkoxylated polycarboxylates, polymers of unsaturated monomeric acids, polyethylene glycols, styrene co-polymers, cellulose sulfate esters, carboxylated polysaccharides, amphiphilic graft copolymers and sulfonated polymers.

The performance polymers may be included to provide benefits in one or more of the areas of spotting and filming, dispersancy, cleaning and bleachable stain cleaning. The performance polymers which provide a dispersancy benefit can also be referred to as dispersing polymers.

A preferred performance polymer for use herein, in terms of cleaning of bleachable stains enhancing is an alkoxylated polyalkyleneimine.

Alkoxylated Polyalkyleneimine

The alkoxylated polyalkyleneimine has a polyalkyleneimine backbone and alkoxy chains. Preferably the polyalkyleneimine is polyethyleneimine. Preferably, the alkoxylated polyalkyleneimine is not quaternized.

In a preferred alkoxylated polyalkyleneimine for use in the composition of the invention:
  i) the polyalkyleneimine backbone represents from 0.5% to 40%, preferably from 1% to 30% and especially from 2% to 20% by weight of the alkoxylated polyalkyleneimine; and
  ii) the alkoxy chains represent from 60% to 99%, preferably from 50% to about 95%, more preferably from 60% to 90% by weight of the alkoxylated polyalkyleneimine
  Preferably, the alkoxy chains have an average of from about 1 to about 50, more preferably from about 2 to about 40, more preferably from about 3 to about 30 and especially from about 3 to about 20 and even more especially from about 4 to about 15 alkoxy units preferably ethoxy units. In other suitable polyalkyleneimine for use herein, the alkoxy chains have an average of from about 0 to 30, more preferably from about 1 to about 12, especially from about 1 to about 10 and even more especially from about 1 to about 8 propoxy units. Especially preferred are alkoxylated polyethyleneimines wherein the alkoxy chains comprise a combination of ethoxy and propoxy chains, in particular polyethyleneimines comprising chains of from 4 to 20 ethoxy units and from 0 to 6 propoxy units.

Preferably, the alkoxylated polyalkyleneimine is obtained from alkoxylation wherein the starting polyalkyleneimine has a weight-average molecular weight of from about 100 to about 60,000, preferably from about 200 to about 40,000, more preferably from about 300 to about 10,000 g/mol. A preferred example is 600 g/mol polyethyleneimine core ethoxylated to 20 EO groups per NH and is available from BASF.

Other suitable polyalkyleneimines for use herein includes compounds having the following general structure: bis $((C_2H_5O)(C_2H_4O)_n)(CH_3)-N^+-C_xH_{2x}-N^+-(CH_3)$-bis $((C_2H_5O)(C_2H_4O)_n)$, wherein n=from 20 to 30, and x=from 3 to 8, or sulphated or sulphonated variants thereof.

Polycarboxylates

For example, a wide variety of modified or unmodified polyacrylates, polyacrylate/maleates, or polyacrylate/methacrylates are highly useful. It is believed, though it is not intended to be limited by theory, that these performance polymers are excellent dispersing agents and enhance overall detergent performance, particularly when used in combination with buffering agents, by crystal growth inhibition, particulate soil release peptization, and entire deposition. Examples of polymeric dispersing agents are found in U.S. Pat. No. 3,308,067 and EP 193,360.

Suitable polycarboxylate-based polymers include polycarboxylate polymers that may have average molecular weights of from about 500 Da to about 500,000 Da, or from about 1,000 Da to about 100,000 Da, or even from about 3,000 Da to about 80,000 Da. In one aspect, suitable polycarboxylates may be selected from the group comprising polymers comprising acrylic acid such as Sokalan PA30, PA20, PA15, PA10 and sokalan CP10 (BASF GmbH, Ludwigshafen, Germany), Acusol™ 45N, 480N, 460N and 820 (sold by Rohm and Haas, Philadelphia, Pa., USA) polyacrylic acids, such as Acusol™ 445 and Acusol™ 420 (sold by Rohm and Haas, Philadelphia, Pa., USA) acrylic/maleic co-polymers, such as Acusol™ 425N and acrylic/methacrylic copolymers Several examples of such polymers are disclosed in WO 95/01416.

Alkoxylated polycarboxylates such as those prepared from polyacrylates are useful herein to and can provide additional grease suspension. Such materials are described in WO 91/08281 and PCT 90/01815. Chemically, these materials comprise polyacrylates having one ethoxy sidechain per every 7-8 acrylate units. The side-chains are ester-linked to the polyacrylate "backbone" to provide a "comb" polymer type structure. The molecular weight can vary, but may be in the range of about 2000 to about 50,000.

Dispersant polymers suitable for use herein are further illustrated by the film-forming polymers described in U.S. Pat. No. 4,379,080 (Murphy), issued Apr. 5, 1983.

Other suitable dispersing polymers include those disclosed in U.S. Pat. No. 3,308,067 issued Mar. 7, 1967, to Diehl. Unsaturated monomeric acids that can be polymerized to form suitable dispersing polymers include acrylic acid, maleic acid (or maleic anhydride), fumaric acid, itaconic acid, aconitic acid, mesaconic acid, citraconic acid and methylenemalonic acid. The presence of monomeric segments containing no carboxylate radicals such as methyl vinyl ether, styrene, ethylene, etc. is suitable provided that such segments do not constitute more than about 50% by weight of the dispersing polymer.

Co-polymers of acrylamide and acrylate having a molecular weight of from about 3,000 to about 100,000, preferably from about 4,000 to about 20,000, and an acrylamide content of less than about 50%, preferably less than about 20%, by weight of the dispersing polymer can also be used. Most preferably, such dispersing polymer has a molecular weight of from about 4,000 to about 20,000 and an acrylamide content of from about 0% to about 15%, by weight of the polymer.

Yet other dispersing polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate is the most preferred polymer of this group.

Other suitable dispersing polymers are the carboxylated polysaccharides, particularly starches, celluloses and alginates, described in U.S. Pat. No. 3,723,322, Diehl, issued Mar. 27, 1973; the dextrin esters of polycarboxylic acids disclosed in U.S. Pat. No. 3,929,107, Thompson, issued Nov. 11, 1975; the hydroxyalkyl starch ethers, starch esters, oxidized starches, dextrins and starch hydrolysates described in U.S. Pat. No. 3,803,285, Jensen, issued Apr. 9, 1974; the carboxylated starches described in U.S. Pat. No. 3,629,121, Eldib, issued Dec. 21, 1971; and the dextrin starches described in U.S. Pat. No. 4,141,841, McDonald, issued Feb. 27, 1979.

Preferred cellulose-derived dispersant polymers are the carboxymethyl celluloses.

Yet another group of acceptable dispersing are the organic dispersing polymers, such as polyaspartates.

Amphiphilic Graft Co-Polymers

Suitable amphilic graft co-polymer comprises (i) polyethylene glycol backbone; and (ii) and at least one pendant moiety selected from polyvinyl acetate, polyvinyl alcohol and mixtures thereof. In other examples, the amphilic graft copolymer is Sokalan HP22, supplied from BASF.

Sulfonated Polymers

Suitable sulfonated/carboxylated polymers described herein may have a weight average molecular weight of less than or equal to about 100,000 Da, preferably less than or equal to about 75,000 Da, more preferably less than or equal to about 50,000 Da, more preferably from about 3,000 Da to about 50,000, and specially from about 5,000 Da to about 45,000 Da.

Preferred carboxylic acid monomers include one or more of the following: acrylic acid, maleic acid, itaconic acid, methacrylic acid, or ethoxylate esters of acrylic acids, acrylic and methacrylic acids being more preferred. Preferred sulfonated monomers include one or more of the following: sodium (meth) allyl sulfonate, vinyl sulfonate, sodium phenyl (meth) allyl ether sulfonate, or 2-acrylamido-methyl propane sulfonic acid. Preferred non-ionic monomers include one or more of the following: methyl (meth) acrylate, ethyl (meth) acrylate, t-butyl (meth) acrylate, methyl (meth) acrylamide, ethyl (meth) acrylamide, t-butyl (meth) acrylamide, styrene, or α-methyl styrene.

In the polymers, all or some of the carboxylic or sulfonic acid groups can be present in neutralized form, i.e. the acidic hydrogen atom of the carboxylic and/or sulfonic acid group in some or all acid groups can be replaced with metal ions, preferably alkali metal ions and in particular with sodium ions.

Preferred commercial available polymers include: Alcosperse 240, Aquatreat AR 540 and Aquatreat MPS supplied by Alco Chemical; Acumer 3100, Acumer 2000, Acusol 587G and Acusol 588G supplied by Rohm & Haas; Goodrich K-798, K-775 and K-797 supplied by BF Goodrich; and ACP 1042 supplied by ISP technologies Inc. Particularly preferred polymers are Acusol 587G and Acusol 588G supplied by Rohm & Haas, Versaflex Si™ (sold by Alco Chemical, Tennessee, USA) and those described in U.S. Pat. No. 5,308,532 and in WO 2005/090541.

Suitable styrene co-polymers may be selected from the group comprising, styrene co-polymers with acrylic acid and optionally sulphonate groups, having average molecular weights in the range 1,000-50,000, or even 2,000-10,000 such as those supplied by Alco Chemical Tennessee, USA, under the tradenames Alcosperse® 729 and 747.

Non-Ionic Surfactants

Suitable for use herein are non-ionic surfactants, they can acts as anti-redeposition agents. Traditionally, non-ionic surfactants have been used in automatic dishwashing for surface modification purposes in particular for sheeting to avoid filming and spotting and to improve shine. It has been found that in the compositions of the invention, where filming and spotting does not seem to be a problem, non-ionic surfactants can contribute to prevent redeposition of soils.

Preferably, the composition comprises a non-ionic surfactant or a non-ionic surfactant system having a phase inversion temperature, as measured at a concentration of 1% in distilled water, between 40 and 70° C., preferably between 45 and 65° C. By a "non-ionic surfactant system" is meant herein a mixture of two or more non-ionic surfactants. Preferred for use herein are non-ionic surfactant systems. They seem to have improved cleaning and finishing properties and stability in product than single non-ionic surfactants.

Phase inversion temperature is the temperature below which a surfactant, or a mixture thereof, partitions preferentially into the water phase as oil-swollen micelles and above which it partitions preferentially into the oil phase as water swollen inverted micelles. Phase inversion temperature can be determined visually by identifying at which temperature cloudiness occurs.

The phase inversion temperature of a non-ionic surfactant or system can be determined as follows: a solution containing 1% of the corresponding surfactant or mixture by weight of the solution in distilled water is prepared. The solution is stirred gently before phase inversion temperature analysis to ensure that the process occurs in chemical equilibrium. The phase inversion temperature is taken in a thermostable bath by immersing the solutions in 75 mm sealed glass test tube. To ensure the absence of leakage, the test tube is weighed before and after phase inversion temperature measurement. The temperature is gradually increased at a rate of less than 1° C. per minute, until the temperature reaches a few degrees below the pre-estimated phase inversion temperature. Phase inversion temperature is determined visually at the first sign of turbidity.

Suitable nonionic surfactants include: i) ethoxylated non-ionic surfactants prepared by the reaction of a monohydroxy alkanol or alkyphenol with 6 to 20 carbon atoms with preferably at least 12 moles particularly preferred at least 16 moles, and still more preferred at least 20 moles of ethylene oxide per mole of alcohol or alkylphenol; ii) alcohol alkoxylated surfactants having a from 6 to 20 carbon atoms and at least one ethoxy and propoxy group. Preferred for use herein are mixtures of surfactants i) and ii).

Another suitable non-ionic surfactants are epoxy-capped poly(oxyalkylated) alcohols represented by the formula:

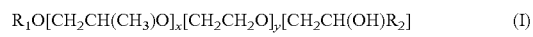

$$R_1O[CH_2CH(CH_3)O]_x[CH_2CH_2O]_y[CH_2CH(OH)R_2] \quad (I)$$

wherein $R_1$ is a linear or branched, aliphatic hydrocarbon radical having from 4 to 18 carbon atoms; $R_2$ is a linear or branched aliphatic hydrocarbon radical having from 2 to 26 carbon atoms; x is an integer having an average value of from 0.5 to 1.5, more preferably about 1; and y is an integer having a value of at least 15, more preferably at least 20.

Preferably, the surfactant of formula I has at least about 10 carbon atoms in the terminal epoxide unit $[CH_2CH(OH)R_2]$. Suitable surfactants of formula I are Olin Corporation's POLY-TERGENT® SLF-18B nonionic surfactants, as described, for example, in WO 94/22800, published Oct. 13, 1994 by Olin Corporation.

Preferably non-ionic surfactants and/or system to use as anti-redeposition agents herein have a Draves wetting time of less than 360 seconds, preferably less than 200 seconds, more preferably less than 100 seconds and especially less than 60 seconds as measured by the Draves wetting method (standard method ISO 8022 using the following conditions; 3-g hook, 5-g cotton skein, 0.1% by weight aqueous solution at a temperature of 25° C.).

Amine oxides surfactants are also useful in the present invention as anti-redeposition surfactants include linear and branched compounds having the formula:

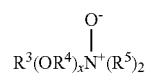

$$R^3(OR^4)_xN^+(R^5)_2 \quad O^-$$

wherein $R^3$ is selected from an alkyl, hydroxyalkyl, acylamidopropoyl and alkyl phenyl group, or mixtures thereof, containing from 8 to 26 carbon atoms, preferably 8 to 18 carbon atoms; $R^4$ is an alkylene or hydroxyalkylene group containing from 2 to 3 carbon atoms, preferably 2 carbon atoms, or mixtures thereof; x is from 0 to 5, preferably from 0 to 3; and each $R^5$ is an alkyl or hydroxyalkyl group containing from 1 to 3, preferably from 1 to 2 carbon atoms, or a polyethylene oxide group containing from 1 to 3, preferable 1, ethylene oxide groups. The $R^5$ groups can be attached to each other, e.g., through an oxygen or nitrogen atom, to form a ring structure.

These amine oxide surfactants in particular include $C_{10}$-$C_{18}$ alkyl dimethyl amine oxides and $C_8$-$C_{18}$ alkoxy ethyl dihydroxyethyl amine oxides. Examples of such materials include dimethyloctylamine oxide, diethyldecylamine oxide, bis-(2-hydroxyethyl)dodecylamine oxide, dimethyldodecylamine oxide, dipropyltetradecylamine oxide, methylethylhexadecylamine oxide, dodecylamidopropyl dimethylamine oxide, cetyl dimethylamine oxide, stearyl dimethylamine oxide, tallow dimethylamine oxide and dimethyl-2-hydroxyoctadecylamine oxide. Preferred are $C_{10}$-$C_{18}$ alkyl dimethylamine oxide, and $C_{10\text{-}18}$ acylamido alkyl dimethylamine oxide.

Non-ionic surfactants may be present in amounts from 0 to 10%, preferably from 0.1% to 10%, and most preferably from 0.25% to 6% by weight of the composition.

Anionic Surfactant

Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate so as to form a water-soluble compound. Usually, the hydrophobic group will comprise a C8-C 22 alkyl, or acyl group. Such surfactants are employed in the form of water-soluble salts and the salt-forming cation usually is selected from sodium, potassium, ammonium, magnesium and mono-, di- or tri-C 2-C 3 alkanolammonium, with the sodium cation being the usual one chosen.

The anionic surfactant can be a single surfactant or a mixture of anionic surfactants. Preferably the anionic surfactant comprises a sulphate surfactant, more preferably a sulphate surfactant selected from the group consisting of alkyl sulphate, alkyl alkoxy sulphate and mixtures thereof. Preferred alkyl alkoxy sulphates for use herein are alkyl ethoxy sulphates.

Alkyl Ether Sulphate (AES) Surfactants

The alkyl ether sulphate surfactant has the general formula (I)

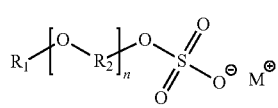

(I)

having an average alkoxylation degree (n) of from about 0.1 to about 8, 0.2 to about 5, even more preferably from about 0.3 to about 4, even more preferably from about 0.8 to about 3.5 and especially from about 1 to about 3.

The alkoxy group ($R_2$) could be selected from ethoxy, propoxy, butoxy or even higher alkoxy groups and mixtures thereof. Preferably, the alkoxy group is ethoxy. When the alkyl ether sulphate surfactant is a mixture of surfactants, the alkoxylation degree is the weight average alkoxylation degree of all the components of the mixture (weight average alkoxylation degree). In the weight average alkoxylation degree calculation the weight of alkyl ether sulphate surfactant components not having alkoxylated groups should also be included.

Weight average alkoxylation degree
$n=(x1*\text{alkoxylation degree of surfactant } 1+x2*\text{alkoxylation degree of surfactant } 2+\ldots)/(x1+x2+\ldots)$ wherein x1, x2, are the weights in grams of each alkyl ether sulphate surfactant of the mixture and alkoxylation degree is the number of alkoxy groups in each alkyl ether sulphate surfactant.

The hydrophobic alkyl group ($R_1$) can be linear or branched. Most suitable the alkyl ether sulphate surfactant to be used in the detergent of the present invention is a branched alkyl ether sulphate surfactant having a level of branching of from about 5% to about 40%, preferably from about 10% to about 35% and more preferably from about 20% to about 30%. Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the alkyl ether sulphate surfactant used in the detergent of the invention.

The branched alkyl ether sulphate surfactant can be a single sulphate surfactant or a mixture of sulphate surfactants. In the case of a single sulphate surfactant the percentage of branching refers to the weight percentage of the hydrocarbyl chains that are branched in the original alcohol from which the sulphate surfactant is derived.

In the case of a sulphate surfactant mixture the percentage of branching is the weight average and it is defined according to the following formula:

Weight average of branching (%)=$[(x1*\text{wt \% branched alcohol 1 in alcohol } 1+x2*\text{wt \% branched alcohol 2 in alcohol } 2+\ldots)/(x1+x2+\ldots)]*100$ wherein x1, x2, are the weight in grams of each alcohol in the total alcohol mixture of the alcohols which were used as starting material for the AES surfactant for the detergent of the invention. In the weight average branching degree calculation the weight of AES surfactant components not having branched groups should also be included.

Preferably the anionic surfactant of this invention is not purely based on a linear alcohol, but has some alcohol content that contains a degree of branching. Without wishing to be bound by theory it is believed that branched surfactant drives stronger starch cleaning, particularly when used in combination with an α-amylase, based on its surface packing.

Alkyl ether sulphates are commercially available with a variety of chain lengths, ethoxylation and branching degrees, examples are those based on Neodol alcohols ex the Shell company, Lial-Isalchem and Safol ex the Sasol company, natural alcohols ex The Procter & Gamble Chemicals company.

Preferably, the alkyl ether sulfate is present from about 0.05% to about 20%, preferably from about 0.1% to about 10%, more preferably from about 1% to about 6%, and most preferably from about 2% to about 5% by weight of the composition.

Suds Suppressor

Suds suppressors suitable for use herein include an alkyl phosphate ester suds suppressor, a silicone suds suppressor, or combinations thereof. Suds suppressor technology and other defoaming agents useful herein are documented in "Defoaming, Theory and Industrial Applications," Ed., P. R. Garrett, Marcel Dekker, N.Y., 1973, incorporated herein by reference.

Suds suppressors are preferably included in the composition of the invention, especially when the composition comprises anionic surfactant. The suds suppressor is included in the composition at a level of from about 0.0001% to about 10%, preferably from about 0.001% to about 5%, more preferably from about 0.01% to about 1.5% and especially from about 0.01% to about 0.5%, by weight of the composition.

A preferred suds suppressor is a silicone based suds suppressor. Silicone suds suppressor technology and other defoaming agents useful herein are extensively documented in "Defoaming, Theory and Industrial Applications", Ed., P. R. Garrett, Marcel Dekker, N.Y., 1973, ISBN 0-8247-8770-6, incorporated herein by reference. See especially the chapters entitled "Foam control in Detergent Products" (Ferch et al) and "Surfactant Antifoams" (Blease et al). See also U.S. Pat. Nos. 3,933,672 and 4,136,045. A preferred silicone based suds suppressors is polydimethylsiloxanes having trimethylsilyl, or alternate end blocking units as the silicone. These may be compounded with silica and/or with surface-active non-silicon components, as illustrated by a suds suppressor comprising 12% silicone/silica, 18% stearyl alcohol and 70% starch in granular form. A suitable commercial source of the silicone active compounds is Dow Corning Corp. Silicone based suds suppressors are useful in that the silica works well to suppress the foam generated by the soils and surfactant Another suitable silicone based suds suppressor comprises solid silica, a silicone fluid or a silicone resin. The silicone based suds suppressor can be in the form of a granule or a liquid.

Another silicone based suds suppressor comprises dimethylpolysiloxane, a hydrophilic polysiloxane compound having polyethylenoxy-propylenoxy group in the side chain, and a micro-powdery silica.

A phosphate ester suds suppressor may also be used. Suitable alkyl phosphate esters contain from 16-20 carbon atoms. Such phosphate ester suds suppressors may be monostearyl acid phosphate or monooleyl acid phosphate or salts thereof, preferably alkali metal salts.

Other suitable suds suppressors are calcium precipitating fatty acid soaps. However, it has been found to avoid the use of simple calcium-precipitating soaps as antifoams in the present composition as they tend to deposit on dishware. Indeed, fatty acid based soaps are not entirely free of such problems and the formulator will generally choose to minimize the content of potentially depositing antifoams in the instant composition.

Other Enzymes

Preferably the composition of the invention further comprises one or more enzymes selected from the group consisting of an a-amylase, a b-amylase, a pullulanase, a protease, a lipase, a cellulase, an oxidase, a phospholipase, a perhydrolase, a xylanase, a pectate lyase, a pectinase, a galacturanase, a hemicellulase, a xyloglucanase, a mannanase and a mixture thereof.

Suitable enzymes include X-Pect®, Mannaway®, Lipex®, Lipoclean®, Whitezyme®, Carezyme®, Celluzyme®, Carezyme Premium®, Celluclean® from Novozymes A/S and Purastar® and PrimaGreen® from DuPont.

Buffer

The benefits provided by the composition of the invention are linked to the low pH of the wash liquor. It is not sufficient to provide a composition presenting a low pH when dissolved in deionised water what is important is that the low pH of the composition is maintained during the duration of the wash.

In the process of dishwashing, the water and the different ions coming from the soils can destabilise the pH of the composition. In order to maintain the composition at low pH a buffering system capable of maintaining the low pH during the wash is needed. When the composition of the invention is added to water to create a wash liquor the buffer generates a buffering system. A buffering systems can be created either by using a mixture of an acid and its anion, such as a citrate salt and citric acid, or by using a mixture of the acid form (citric acid) with a source of alkalinity (such as a hydroxide, bicarbonate or carbonate salt) or by using the anion (sodium citrate) with a source of acidity (such as sodium bisulphate). Suitable buffering systems comprise mixtures of organic acids and their salts, such as citric acid and citrate.

Preferred buffers for use herein include a polycarboxylic acid, its salts and mixtures thereof, preferably citric acid, citrate and mixtures thereof.

Preferably the composition of the invention comprises from about 1% to about 60%, more preferably from about 10% to about 40% by weight of the composition of a buffer, preferably selected from citric acid, citrate and mixtures thereof.

Builder

Preferably, the composition of the invention is substantially builder free, i.e. comprises less than about 10%, preferably less than about 5%, more preferably less than about 1% and especially less than about 0.1% of builder by weight of the composition. Builders are materials that sequester hardness ions, particularly calcium and/or magnesium. Strong calcium builders are species that are particularly effective at binding calcium and exhibit strong calcium binding constants, particularly at high pHs.

For the purposes of this patent a "builder" is a strong calcium builder. A strong calcium builder can consist of a builder that when present at 0.5 mM in a solution containing 0.05 mM of Fe(III) and 2.5 mM of Ca(II) will selectively bind the calcium ahead of the iron at one or more of pHs 6.5 or 8 or 10.5. Specifically, the builder when present at 0.5 mM in a solution containing 0.05 mM of Fe(III) and 2.5 mM of Ca(II) will bind less than 50%, preferably less than 25%, more preferably less than 15%, more preferably less than 10%, more preferably less than 5%, more preferably less than 2% and specially less than 1% of the Fe(III) at one or preferably more of pHs 6.5 or 8 as measured at 25° C. The builder will also preferably bind at least 0.25 mM of the calcium, preferably at least 0.3 mM, preferably at least 0.4 mM, preferably at least 0.45 mM, preferably at least 0.49 mM of calcium at one or more of pHs 6.5 or 8 or 10.5 as measured at 25° C.

The most preferred strong calcium builders are those that will bind calcium with a molar ratio (builder:calcium) of less than 2.5:1, preferably less than 2:1, preferably less than 1.5:1 and most preferably as close as possible to 1:1, when equal quantities of calcium and builder are mixed at a concentration of 0.5 mM at one or more of pHs 6.5 or 8 or 10.5 as measured at 25° C.

Examples of strong calcium builders include phosphate salts such as sodium tripolyphosphate, amino acid-based builders such as amino acid based compounds, in particular MGDA (methyl-glycine-diacetic acid), and salts and derivatives thereof, GLDA (glutamic-N,N-diacetic acid) and salts and derivatives thereof, IDS (iminodisuccinic acid) and salts and derivatives thereof, carboxy methyl inulin and salts and derivatives thereof and mixtures thereof.

Other builders include amino acid based compound or a succinate based compound. Other suitable builders are described in U.S. Pat. No. 6,426,229. In one aspect, suitable builders include; for example, aspartic acid-N-monoacetic acid (ASMA), aspartic acid-, -diacetic acid (ASDA), aspartic acid-N-monopropionic acid (ASMP), iminodisuccinic acid (IDA), N-(2-sulfomethyl) aspartic acid (SMAS), N-(2- sulfoethyl) aspartic acid (SEAS), N-(2-sulfomethyl) glutamic acid (SMGL), N-(2-sulfoethyl) glutamic acid (SEGL), N-methyliminodiacetic acid (MID A), alpha-alanine-N,N-diacetic acid (alpha-ALDA), serine-, -diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA) and sulfomethyl-N,N-diacetic acid (SMDA) and alkali metal salts or ammonium salts thereof.

Polycarboxylic acids and their salts do not act as builders at the pH of the present invention and therefore are not to be considered as builder within the meaning of the invention. Polycarboxylic acids and their salts are considered a buffer within the meaning of the invention.

Iron Chelant

The composition of the invention preferably comprises an iron chelant at a level of from about 0.1% to about 5%, preferably from about 0.2% to about 2%, more preferably from about 0.4% to about 1% by weight of the composition.

As commonly understood in the detergent field, chelation herein means the binding or complexation of a bi- or multi-dentate ligand. These ligands, which are often organic compounds, are called chelants, chelators, chelating agents, and/or sequestering agent. Chelating agents form multiple bonds with a single metal ion. Chelants form soluble, complex molecules with certain metal ions, inactivating the ions so that they cannot normally react with other elements or ions to produce precipitates or scale. The ligand forms a chelate complex with the substrate. The term is reserved for complexes in which the metal ion is bound to two or more atoms of the chelant.

The composition of the present invention is preferably substantially free of builders and preferably comprises an iron chelant. An iron chelant has a strong affinity (and high binding constant) for Fe(III).

It is to be understood that chelants are to be distinguished from builders. For example, chelants are exclusively organic and can bind to metals through their N,P,O coordination sites or mixtures thereof while builders can be organic or inorganic and, when organic, generally bind to metals through their O coordination sites. Moreover, the chelants typically bind to transition metals much more strongly than to calcium and magnesium; that is to say, the ratio of their transition metal binding constants to their calcium/magnesium binding constants is very high. By contrast, builders herein exhibit much less selectivity for transition metal binding, the above-defined ratio being generally lower.

The chelant in the composition of the invention is a selective strong iron chelant that will preferentially bind with iron (III) versus calcium in a typical wash environment where calcium will be present in excess versus the iron, by a ratio of at least 10:1, preferably greater than 20:1.

The iron chelant when present at 0.5 mM in a solution containing 0.05 mM of Fe(III) and 2.5 mM of Ca(II) will fully bind at least 50%, preferably at least 75%, more preferably at least 85%, more preferably at least 90%, more preferably at least 95%, more preferably at least 98% and specially at least 99% of the Fe(III) at one or preferably more of pHs 6.5 or 8 as measured at 25° C. The amount of Fe(III) and Ca(II) bound by a builder or chelant is determined as explained herein below Method for Determining Competitive Binding To determine the selective binding of a specific ligand to specific metal ions, such as iron(III) and calcium (II), the binding constants of the metal ion-ligand complex are obtained via reference tables if available, otherwise they are determined experimentally. A speciation modeling simulation can then be performed to quantitatively determine what metal ion-ligand complex will result under a specific set of conditions.

As used herein, the term "binding constant" is a measurement of the equilibrium state of binding, such as binding between a metal ion and a ligand to form a complex. The binding constant $K_{bc}$ (25° C. and an ionic strength (I) of 0.1 mol/L) is calculated using the following equation:

$$K_{bc}=[ML_x]/([M][L]^x)$$

where [L] is the concentration of ligand in mol/L, x is the number of ligands that bond to the metal, [M] is the concentration of metal ion in mol/L, and [ML$_x$] is the concentration of the metal/ligand complex in mol/L.

Specific values of binding constants are obtained from the public database of the National Institute of Standards and Technology ("NIST"), R. M. Smith, and A. E. Martell, NIST Standard Reference Database 46, NIST Critically Selected Stability Constants of Metal Complexes: Version 8.0, May 2004, U.S. Department of Commerce, Technology Administration, NIST, Standard Reference Data Program, Gaithersburg, Md. If the binding constants for a specific ligand are not available in the database then they are measured experimentally.

Once the appropriate binding constants have been obtained, a speciation modeling simulation can be performed to quantitatively determine what metal ion-ligand complex will result under a specific set of conditions including ligand concentrations, metal ion concentrations, pH, temperature and ionic strength. For simulation purposes, NIST values at 25° C. and an ionic strength (I) of 0.1 mol/L with sodium as the background electrolyte are used. If no value is listed in NIST the value is measured experimentally. PHREEQC from the US Geological Survey, http://wwwbr-r.cr.usgs.gov/projects/GWC_coupled/phreeqc/. PHREEQC is used for speciation modeling simulation.

Iron chelants include those selected from siderophores, catechols, enterobactin, hydroxamates and hydroxypyridinones or hydroxypyridine N-Oxides. Preferred chelants include anionic catechols, particularly catechol sulphonates, hydroxamates and hydroxypyridine N-Oxides. Preferred strong chelants include hydroxypyridine N-Oxide (HPNO), Octopirox, and/or Tiron (disodium 4,5-dihydroxy-1,3-benzenedisulfonate), with Tiron, HPNO and mixtures thereof as the most preferred for use in the composition of the invention. HPNO within the context of this invention can be substituted or unsubstituted. Numerous potential and actual resonance structures and tautomers can exist. It is to be understood that a particular structure includes all of the reasonable resonance structures and tautomers.

Bleach

The composition of the invention preferably comprises less than about 20% bleach, more preferably less than 10% and especially from about 1 to about 5% bleach by weight of the composition.

Inorganic and organic bleaches are suitable for use herein. Inorganic bleaches include perhydrate salts such as perborate, percarbonate, perphosphate, persulfate and persilicate salts. The inorganic perhydrate salts are normally the alkali metal salts. The inorganic perhydrate salt may be included as the crystalline solid without additional protection. Alternatively, the salt can be coated. Suitable coatings include sodium sulphate, sodium carbonate, sodium silicate and mixtures thereof. Said coatings can be applied as a mixture applied to the surface or sequentially in layers.

Alkali metal percarbonates, particularly sodium percarbonate is the preferred bleach for use herein. The percarbonate is most preferably incorporated into the products in a coated form which provides in-product stability.

Potassium peroxymonopersulfate is another inorganic perhydrate salt of utility herein.

Typical organic bleaches are organic peroxyacids, especially diperoxydodecanedioc acid, diperoxytetradecanedioc acid, and diperoxyhexadecanedioc acid. Mono- and diperazelaic acid, mono- and diperbrassylic acid are also suitable herein. Diacyl and Tetraacylperoxides, for instance dibenzoyl peroxide and dilauroyl peroxide, are other organic peroxides that can be used in the context of this invention.

Further typical organic bleaches include the peroxyacids, particular examples being the alkylperoxy acids and the arylperoxy acids. Preferred representatives are (a) peroxybenzoic acid and its ring-substituted derivatives, such as alkylperoxybenzoic acids, but also peroxy-α-naphthoic acid and magnesium monoperphthalate, (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates, and (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi (6-aminopercaproic acid). Preferably, the level of bleach in the composition of the invention is from about 0 to about 10%, more preferably from about 0.1 to about 5%, even more preferably from about 0.5 to about 3% by weight of the composition.

Crystal Growth Inhibitor

Crystal growth inhibitors are materials that can bind to calcium carbonate crystals and prevent further growth of species such as aragonite and calcite.

Examples of effective crystal growth inhibitors include phosphonates, polyphosphonates, inulin derivatives and cyclic polycarboxylates.

Suitable crystal growth inhibitors may be selected from the group comprising HEDP (1-hydroxyethylidene 1,1-diphosphonic acid), carboxymethylinulin (CMI), tricarballylic acid and cyclic carboxylates. For the purposes of this invention the term carboxylate covers both the anionic form and the protonated carboxylic acid form.

Cyclic carboxylates contain at least two, preferably three or preferably at least four carboxylate groups and the cyclic structure is based on either a mono- or bi-cyclic alkane or a heterocycle. Suitable cyclic structures include cyclopropane, cyclobutane, cyclohexane or cyclopentane or cycloheptane, bicyclo-heptane or bicyclo-octane and/or tetrhaydrofuran. One preferred crystal growth inhibitor is cyclopentane tetracarboxylate.

Cyclic carboxylates having at least 75%, preferably 100% of the carboxylate groups on the same side, or in the "cis" position of the 3D-structure of the cycle are preferred for use herein.

It is preferred that the two carboxylate groups, which are on the same side of the cycle are in directly neighbouring or "ortho" positions Preferred crystal growth inhibitors include HEDP, tricarballylic acid, tetrahydrofurantetracarboxylic acid (THFTCA) and cyclopentanetetracarboxylic acid (CPTCA). The THFTCA is preferably in the 2c,3t,4t,5c-configuration, and the CPTCA in the cis,cis,cis,cis-configuration.

The crystal growth inhibitors are present preferably in a quantity from about 0.01 to about 10%, particularly from about 0.02 to about 5% and in particular from 0.05 to 3% by weight of the composition.

Preferred proteases for use herein have an isoelectric point of from about 4 to about 9, preferably from about 4 to about 8, most preferably from about 4.5 to about 6.5. Proteases with this isoelectric point present good activity in the wash liquor provided by the composition of the invention. As used herein, the term "isoelectric point" refers to electrochemical properties of an enzyme such that the enzyme has a net charge of zero as calculated by the method described below.

Preferably the protease of the composition of the invention is an endoprotease, by "endoprotease" is herein understood a protease that breaks peptide bonds of non-terminal amino acids, in contrast with exoproteases that break peptide bonds from their end-pieces.

Isoelectric Point

The isoelectric point (referred to as IEP or pI) of an enzyme as used herein refers to the theoretical isoelectric point as measured according to the online pI tool available from ExPASy server at the following web address:
http://web.expasy.org/compute_pi/

The method used on this site is described in the below reference:

Gasteiger E., Hoogland C., Gattiker A., Duvaud S., Wilkins M. R., Appel R. D., Bairoch A.; Protein Identification and Analysis Tools on the ExPASy Server;
(In) John M. Walker (ed): The Proteomics Protocols Handbook, Humana Press (2005).

Preferred proteases for use herein are selected from the group consisting of:
 (vi) a metalloprotease;
 (vii) a cysteine protease;
 (viii) a neutral serine protease;
 (ix) an aspartate protease, and
 (x) mixtures thereof.

Suitable proteases include those of animal, vegetable or microbial origin. Preferred proteases may be of microbial origin. The suitable proteases include chemically or genetically modified mutants of the aforementioned suitable proteases.

Metalloproteases

Metalloproteases can be derived from animals, plants, bacteria or fungi. Suitable metalloprotease can be selected from the group of neutral metalloproteases and

*Myxobacter* metalloproteases. Suitable metalloproteases can include collagenases, hemorrhagic toxins from snake venoms and thermolysin from bacteria.

Preferred thermolysin enzyme variants include an M4 peptidase, more preferably the thermolysin enzyme variant is a member of the PepSY~Peptidase_M4~Peptidase_M4_C family.

Suitable metalloprotease variants can have at least 50% identity to the thermolysin set forth in SEQ ID NO: 1. In some embodiments, the thermolysin enzyme variant is from a genus selected from the group consisting of *Bacillus, Geobacillus, Alicyclobacillus, Lactobacillus, Exiguobacterium, Brevibacillus, Paenibacillus, Herpetosiphon, Oceanobacillus, Shewanella, Clostridium, Staphylococcus, Flavobacterium, Stigmatella, Myxococcus, Vibrio, Methanosarcina, Chryseobacterium, Streptomyces, Kribbella, Janibacter, Nocardioides, Xanthamonas, Micromonospora, Burkholderia, Dehalococcoides, Croceibacter, Kordia, Microscilla, Thermoactinomyces, Chloroflexus, Listeria, Plesiocystis, Haliscomenobacter, Cytophaga,*

*Hahella, Arthrobacter, Brachybacterium, Clavibacter, Microbacterium, Intrasporangium, Frankia, Meiothermus, Pseudomonas, Ricinus, Catenulispora, Anabaena, Nostoc, Halomonas, Chromohalobacter, Bordetella, Variovorax, Dickeya, Pectobacterium, Citrobacter, Enterobacter, Salmonella, Erwinia, Pantoea, Rahnella, Serratia, Geodermatophilus, Gemmata, Xenorhabdus, Photorhabdus, Aspergillus, Neosartorya, Pyrenophora, Saccharopolyspora, Nectria, Gibberella, Metarhizium, Waddlia, Cyanothece, Cellulphaga, Providencia, Bradyrhizobium, Agrobacterium, Mucilaginibacter, Serratia, Sorangium, Streptosporangium, Renibacterium, Aeromonas, Reinekea, Chromobacterium, Moritella, Haliangium, Kangiella, Marinomonas, Vibrionales, Listonella, Salinivibrio, Photobacterium, Alteromonadales, Legionella, Teredinibacter, Reinekea, Hydrogenivirga* and *Pseudoalteromonas*. In some embodiments, the thermolysin enzyme variant is from a genus selected from the group consisting of *Bacillus, Geobacillus, Alicyclobacillus, Lactobacillus, Exiguobacterium, Brevibacillus, Paenibacillus, Herpetosiphon, Oceanobacillus, Shewanella, Clostridium, Staphylococcus, Flavobacterium, Stigmatella, Myxococcus, Vibrio, Methanosarcina, Chryseobacterium*, and *Pseudoalteromonas*. Preferably the thermolysin enzyme is from the genus *Bacillus*.

Preferred metalloproteases include thermolysin, matrix metalloproteinases and those metalloproteases derived from *Bacillus subtilis, Bacillus thermoproteolyticus, Geobacillus stearothermophilus* or *Geobacillus* sp., or *Bacillus amyloliquefaciens*, as described in US PA 2008/0293610A1. A specially preferred metalloprotease belongs to the family EC3.4.24.27.

Further suitable metalloproteases are the thermolysin variants described in WO2014/71410. In one aspect the metalloprotease is a variant of a parent protease, said parent protease having at least 60%, or 80%, or 85% or 90% or 95% or 96% or 97% or 98% or 99% or even 100% identity to SEQ ID NO:1 including those with substitutions at one or more of the following sets of positions versus SEQ ID NO:1:

(a) 2, 26, 47, 53, 87, 91, 96, 108, 118, 154, 179, 197, 198, 199, 209, 211, 217, 219, 225, 232, 256, 257, 259, 261, 265, 267, 272, 276, 277, 286, 289, 290, 293, 295, 298, 299, 300, 301, 303, 305, 308, 311 and 316

(b) 1, 4, 17, 25, 40, 45, 56, 58, 61, 74, 86, 97, 101, 109, 149, 150, 158, 159, 172, 181, 214, 216, 218, 221, 222, 224, 250, 253, 254, 258, 263, 264, 266, 268, 271, 273, 275, 278, 279, 280, 282, 283, 287, 288, 291, 297, 302, 304, 307 and 312;

(c) 5, 9, 11, 19, 27, 31, 33, 37, 46, 64, 73, 76, 79, 80, 85, 89, 95, 98, 99, 107, 127, 129, 131, 137, 141, 145, 148, 151, 152, 155, 156, 160, 161, 164, 168, 171, 176, 180, 182, 187, 188, 205, 206, 207, 210, 212, 213, 220, 227, 234, 235, 236, 237, 242, 244, 246, 248, 249, 252, 255, 270, 274, 284, 294, 296, 306, 309, 310, 313, 314 and 315;

(d) 3, 6, 7, 20, 23, 24, 44, 48, 50, 57, 63, 72, 75, 81, 92, 93, 94, 100, 102, 103, 104, 110, 117, 120, 134, 135, 136, 140, 144, 153, 173, 174, 175, 178, 183, 185, 189, 193, 201, 223, 230, 238, 239, 241, 247, 251, 260, 262, 269, and 285;

(e) 17, 19, 24, 25, 31, 33, 40, 48, 73, 79, 80, 81, 85, 86, 89, 94, 109, 117, 140, 141, 150, 152, 153, 158, 159, 160, 161, 168, 171, 174, 175, 176, 178, 180, 181, 182, 183, 189, 205, 206, 207, 210, 212, 213, 214, 218, 223, 224, 227, 235, 236, 237, 238, 241, 244, 246, 248, 249, 250, 251, 252, 253, 254, 255, 258, 259, 260, 261, 262, 266, 268, 269, 270, 271, 272, 273, 274, 276, 278, 279, 280, 282, 283, 294, 295, 296, 297, 300, 302, 306, 310 and 312;

(f) 1, 2, 127, 128, 180, 181, 195, 196, 197, 198, 199, 211, 223, 224, 298, 299, 300, and 316 all relative to SEQ ID NO:1.

In a further aspect the metalloprotease protease is a variant of a parent protease, said parent protease having at least 60%, or 80%, or 85% or 90% or 95% or 96% or 97% or 98% or 99% or even 100% identity to SEQ ID NO:1 including those with substitutions at one or more of the following sets of positions versus SEQ ID NO:1:

(a) I001L, T002A, T002C, T002I, T002K, T002M, T004K, T004L, T004M, T004Y, Q017L, N037K, F040K, F040L, K045A, K045G, K045M, T049E, T049M, T049Y, L050P, S053C, S053L, A056M, A058E, A058L, Q061L, F063C, A064D, A064E, S065A, S065D, S065E, S065P, S065Y, V087C, V087K, V087L, V087M, V087N, V087Q, V087W, V087Y, N096K, N096L, N096Y, R101H, Q108L, Q108M, G109E, G109M, G109R, G109W, S118A, S118D, S118M, S118Q, S118R, S118T, S118V, Q128A, Q128L, Q128Y, I131L, I137L, T149N, G154A, G154H, G154K, G154M, G154Y, L155M, I164N, N181S, G196A, G196W, I197C, S198A, S198K, G199A, G199Y, A209C, A209M, H216A, Y217C, Y217L, T222K, N227A, I244L, Q246D, V256N, L263A, L263M, T272K, Q273N, Y274M, P277A, P277D, P277Y, L284A, L284M, L284Y, A286K, A286L, A286M, A286N, A286Y, A287C, A288L, A288M, V289A, S291A, S291T, T293A, T293I, T293K, T293L, T293M, T293Y, L295A, L295K, L295M, L295W, Y296M, G297N, S298A, S298G, S298K, S298M, S298R, T299A, T299K, S300D, S300N, Q301K, E302A, V303A, V303P, V303Y, A304E, A304K, A304Y, S305A, S305K, S305M, V306T, V306T, A309C, F310M, D311A, D311K, D311L, D311M, D311V, D311W, D311Y, and A312C;

(b) T002Q, T004V, V007I, V009I, R01IK, I020L, I020V, S025A, S025C, S025K, S025M, S025R, T026C, T026D, Y027C, Y027L, N037L, F040A, A044C, K045F, K045H, K045Q, K045Y, Y046C, R047D, R047E, R047G, R047L, R047M, R047Q, R047T, T049L, T049N, T049Q, T049V, S053A, S053N, S053V, A056E, Q061C, Q061I, A064T, S065L, S065T, S065W, A073F, A073L, A073M, A073W, H074C, H074F, H074M, H074N, H074Q, H074W, T080L, T080N, K085S, N086D, V087R, V087T, L091A, L091N, L091R, L091W, L091Y, S092L, Y093C, N096G, N096H, N096Q, N096R, N096S, N096W, N097E, N097M, A099R, A099S, R101C, R101L, R101S, S102N, S107G, Q108I, Q108K, Q108N, G109S, S118E, M120L, Q128I, Q128K, T129L, T129M, I131W, S134P, G136S, I137E, I137T, I137V, V140D, V148A, V148Q, T149D, T149S, T152G, G154C, G154N, L155I, N159S, N159Y, I164C, I168L, I171G, Y179F, A180S, G189A, Y193F, G196H, G196L, G196Y, I197F, S198M, S198N, S198R, S198W, S201A, A209G, A209I, A209K, A209P, A209R, A209Y, Y211E, Y211R, P214A, P214R, Y217A, Y217F, Y217M, Y217N, K219A, K219E, K219R, K219S, R220A, Y221A, Y221F, Y221G, Y221M, T222A, T222M, Q225C, Q225E, Q225K, Q225L, Q225S, I232L, I232R, I232S, I232T, I232V, I232Y, S234A, S234M, G235A, I236C, I244A, I244M, Q246C, V256S, G257K, G257R, I258A, I258C,

I258K, I258Q, I258V, G259N, G259S, G259T, L263H, L263K, L263N, L263V, G264A, G264N, G264P, G264Q, G264S, G264T, K265N, I266C, I266M, I266T, I266V, F267A, F267C, F267H, F267I, F267K, F267L, F267M, F267T, F267Y, R269K, A270G, L271H, T272A, Q273E, Q273G, L275C, L275Q, L275S, L275T, T276A, T276L, T276V, T276Y, P277E, P277F, P277G, P277H, P277N, P277R, P277V, P277W, S279G, R285Y, A286C, A286Q, A286R, A286T, A288N, V289L, V289M, V289Y, Q290A, Q290H, Q290N, S291V, T293N, T293V, T293W, D294N, L295F, L295G, Y296W, G297D, S298E, S298N, S298P, T299N, S300A, S300G, S300T, Q301M, Q301S, Q301T, Q301V, E302D, E302Q, V303G, V303K, V303L, V303R, V303W, A304R, A304S, A304T, A304W, S305H, S305T, S305V, V306I, Q308A, Q308L, F310C, F310W, D311F, D311G, D311I, D311Q, D311S, D311T, V313C, G314Q, V315L, V315T, K316A, and K316M;

(c) I001K, I001M, I001V, T002F, T002L, T002P, T002S, T002V, T002W, T002Y, T004E, S005D, S005N, S005P, T006C, RO11I, Q017I, Q017W, Q017Y, S025D, S025F, T026K, T026L, T026R, T026V, T026Y, Y027W, Q031A, Q031K, Q031V, N033S, N033T, N037D, N037Q, N037R, F040E, F040G, F040M, F040Q, F040S, F040Y, K045E, K045L, K045S, Y046L, R047A, R047C, R047H, R047K, R047N, T048E, T049A, T049D, T049F, T049H, T049I, T049S, S053F, S053H, S053I, S053M, S053Q, S053T, S053W, A056K, A056Q, A056V, A056W, Q061M, S065I, S065M, S065Q, S065V, D072F, H074E, H074L, Y076H, Y076L, Y076M, Y076Q, V079L, V079Q, V079T, T080I, Y081F, K085E, N086L, N086S, V087D, V087E, V087G, V087I, V087S, L091D, L091E, L091F, L091K, L091M, L091P, L091Q, L091S, Y093T, G095A, G095D, G095H, G095M, G095N, G095S, N096C, N096D, N096I, N096V, N097K, A098C, A098E, A098H, A098R, A099E, A099K, A099P, S107D, Q108C, Q108E, Q108F, Q108H, G127C, G127D, G127E, Q128C, Q128D, Q128E, Q128R, Q128S, T129I, T129R, S134A, I137P, A141S, T145A, T145C, T145E, T145G, T145M, T145N, T145Q, V148L, V148N, V148Y, T149M, T149V, Y151K, T152S, A153T, G154L, G154Q, G154S, G154T, L155C, Q158A, Q158K, Q158M, Q158N, N159R, N159W, S161A, S161N, S161P, S161T, I164L, I164N, I164S, I164T, I164V, I171C, I171E, I171F, I171L, I171S, F172G, F172L, F172M, F172Q, F172S, F172V, F172W, F172Y, G173A, G173C, T174C, V176L, V176N, N181L, G196D, G196E, G196T, I197D, I197K, I197L, I197T, I197V, I197W, I197Y, S198C, S198E, S198F, S198G, S198H, S198I, S198P, S198Q, S198T, S198V, G199C, G199E, G199F, G199H, G199Q, G199S, G199T, G199W, M205L, A209D, A209E, A209L, A209S, A209T, A209V, Y211A, Y211C, Y211D, Y211F, Y211G, Y211H, Y211I, Y211L, Y211N, Y211Q, Y211S, Y211T, D213N, D213S, P214C, P214G, P214K, P214S, H216C, H216E, H216S, H216T, Y217Q, Y217S, Y217T, Y217V, Y217W, S218K, S218L, S218Y, K219D, K219F, K219G, K219H, K219I, K219M, K219N, K219Q, K219T, R220K, R220V, Y221K, Y221N, Y221Q, Y221R, Y221S, Y221T, Y221V, T222C, T222D, T222L, T222Y, T224K, T224M, Q225D, Q225G, Q225H, Q225I, Q225P, Q225V, Q225W, I232C, I232E, I232F, I232K, I232M, I232N, I232Q, I232W, S234D, G235M, I236M, Y242C, Y242F, Y242N, Y242V, I244T, I244V, Q246E, Q246N, Q246T, G247A, G247S, T249K, T249M, T249N, H250A, H250C, G252K, G252Y, V253N, V253T, S254A, S254M, S254R, S254Y, V255L, V255P, V256L, V256T, G257C, G257D, G257E, G257L, G257N, G257P, G257Q, G257S, G257T, G257Y, I258E, I258L, I258M, I258N, G259A, G259C, G259E, G259F, G259H, G259L, G259M, G259W, D261A, D261N, L263C, L263I, L263Q, L263T, K265A, K265C, K265D, K265M, K265P, K265Q, K265S, I266A, I266F, I266L, I266S, F267F, F267G, F267N, F267S, F267V, F267W, Y268M, Y268Q, Y268V, A270C, A270F, A270I, A270L, A270S, L271A, L271D, L271F, L271I, T272E, T272L, T272V, T272W, Q273A, Q273H, Q273Y, Y274F, Y274H, L275I, L275M, L275V, T276C, T276F, T276I, T276P, T276Q, T276W, P277Q, P277S, P277T, T278G, S279A, S279D, S279I, S279L, S279M, S279N, S279Q, S279T, N280A, N280C, N280D, N280E, S282K, S282N, L284V, L284W, R285K, A286D, A286E, A286F, A286G, A286H, A286I, A286S, A287I, A287L, A287N, A287V, A287Y, A288C, A288I, A288S, A288T, A288V, V289C, V289E, V289F, V289G, V289I, V289N, V289S, V289W, Q290C, Q290D, Q290F, Q290G, Q290L, Q290W, S291E, T293C, T293E, T293F, T293G, T293H, T293Q, T293S, L295C, L295I, L295N, Y296N, G297A, G297M, G297R, G297Y, S298C, S298T, S298W, S298Y, T299C, T299F, T299L, T299M, T299R, T299W, S300C, S300K, S300M, S300R, S300Y, Q301E, Q301H, Q301P, Q301R, V303C, V303H, A304C, A304D, A304L, A304N, S305G, S305I, S305L, S305N, S305W, S305Y, V306A, V306S, K307A, K307C, K307G, K307I, K307M, K307N, K307Q, K307R, K307W, K307Y, Q308C, Q308D, Q308F, Q308G, Q308I, Q308M, A309G, A309S, D311C, D311E, A312G, A312M, A312V, V313T, G314A, G314E, G314H, G314M, G314S, G314W, V315A, V315C, V315I, V315M, K316D, K316E, K316F, K316G, K316H, K316L, K316N, K316P, K316Q, K316R, K316S, K316V, K316W and K316Y.

Further suitable metalloproteases are the NprE variants described in WO2007/044993, WO2009/058661 and US 2014/0315775. In one aspect the protease is a variant of a parent protease, said parent protease having at least 45%, or 60%, or 80%, or 85% or 90% or 95% or 96% or 97% or 98% or 99% or even 100% identity to SEQ ID NO:2 including those with substitutions at one or more of the following sets of positions versus SEQ ID NO:2:

S23, Q45, T59, S66, S129, F130, M138, V190, S199, D220, K211, and G222,

Another suitable metalloprotease is a variant of a parent protease, said parent protease having at least 60%, or 80%, or 85% or 90% or 95% or 96% or 97% or 98% or 99% or even 100% identity to SEQ ID NO:2 including those with substitutions at one or more of the following sets of positions versus SEQ ID NO:2:

Q45E, T59P, 566E, S129I, S129V, F130L, M138I, V190I, S199E, D220P, D220E, K211V, K214Q, G222C, M138L/D220P, F130L/D220P, S129I/D220P, V190I/D220P, M138L/V190I/D220P, S129I/V190I, S129V/V190I, S129V/D220P, S129I, F130L/D220P, T004V/S023N, T059K/S66Q/S129I, T059R/S66N/S129I, S129I, F130L/M138L/V190I/D220P and T059K/S66Q/S129V.

Especially preferred metalloproteases for use herein belong to EC classes EC 3.4.22 or EC3.4.24, more preferably they belong to EC classes EC3.4.22.2, EC3.4.24.28 or EC3.4.24.27. The most preferred metalloprotease for use herein belong to EC3.4.24.27.

Suitable commercially available metalloprotease enzymes include those sold under the trade names Neutrase® by Novozymes A/S (Denmark), the Corolase® range including Corolase® 2TS, Corolase® N, Corolase® L10, Corolase® LAP and Corolase® 7089 from AB Enzymes, Protex 14L and Protex 15L from DuPont (Palo Alto, Calif.), those sold as thermolysin from Sigma and the Thermoase range (PC10F and C100) and thermolysin enzyme from Amano enzymes.

Cysteine proteases: Preferably the cysteine proteases of this invention are endoproteases, more preferably selected from bromelain, papain-like proteases and trypsin-like cysteine proteases. Other suitable cysteine proteases can be selected from the group of clostripain, streptopain and clostripain.

Neutral serine proteases: Preferably the serine proteases of this invention are endoproteases. Suitable examples include trypsin-type or chymotrypsin-type proteases, such as trypsin (e.g., of porcine or bovine origin), including the *Fusarium* protease described in U.S. Pat. No. 5,288,627 and the chymotrypsin proteases derived from *Cellumonas* described in US PA 2008/0063774A1.

Aspartate proteases: The aspartate proteases of this invention are preferably derived from bacteria or fungi. In one aspect the microbial aspartic proteases are selected from the group of (i) pepsin-like enzymes produced by *Aspergillus, Penicillium, Rhizopus*, and *Neurospora* and (ii) rennin-like enzymes produced by *Endothia* and *Mucor* spp.

Mixtures of proteases: In one aspect the protease can be a mixture of proteases, either a mix of the proteases mentioned above or a naturally occurring mixture. An example of a naturally occurring mixture is apain derived from the latex of *Carica papaya* fruits.

The composition of the invention preferably comprises from 0.001 to 2%, more preferably from 0.003 to 1%, more preferably from 0.007 to 0.3% and especially from 0.01 to 0.1% by weight of the composition of active protease.

Unit Dose Form

The composition of the invention is suitable to be presented in unit-dose form. Products in unit dose form include tablets, capsules, sachets, pouches, injection moulded containers, etc. Preferred for use herein are tablets and detergents wrapped with a water-soluble film (including wrapped tablets, capsules, sachets, pouches) and injection moulded containers. Preferably the water-soluble film is a polyvinyl alcohol, preferably comprising a bittering agent. The detergent composition of the invention is preferably in the form of a water-soluble multi-compartment pack.

Preferred packs comprise at least two side-by-side compartments superposed onto another compartment. This disposition contributes to the compactness, robustness and strength of the pack and additionally, it minimises the amount of water-soluble packing material required. It only requires three pieces of material to form three compartments. The robustness of the pack allows also for the use of very thin films (less than 150 micron, preferably less than 100 micron) without compromising the physical integrity of the pack. The pack is also very easy to use because the compartments do not need to be folded to be used in machine dispensers of fixed geometry. At least two of the compartments of the pack contain two different compositions. By "different compositions" herein is meant compositions that differ in at least one ingredient.

Preferably, at least one of the compartments contains a solid composition, preferably in powder form and another compartment an aqueous liquid composition, the compositions are preferably in a solid to liquid weight ratio of from about 20:1 to about 1:20, more preferably from about 18:1 to about 2:1 and even more preferably from about 15:1 to about 5:1. This kind of pack is very versatile because it can accommodate compositions having a broad spectrum of values of solid:liquid ratio. Particularly preferred have been found to be pouches having a high solid:liquid ratio because many of the detergent ingredients are most suitable for use in solid form, preferably in powder form. The ratio solid: liquid defined herein refers to the relationship between the weight of all the solid compositions and the weight of all the liquid compositions in the pack.

Preferably the two side-by-side compartments contain liquid compositions, which can be the same but preferably are different and another compartment contains a solid composition, preferably in powder form, more preferably a densified powder. The solid composition contributes to the strength and robustness of the pack.

For dispenser fit reasons the unit dose form products herein preferably have a square or rectangular base and a height of from about 1 to about 5 cm, more preferably from about 1 to about 4 cm. Preferably the weight of the solid composition is from about 5 to about 20 grams, more preferably from about 10 to about 15 grams and the total weight of the liquid compositions is from about 0.5 to about 5 grams, more preferably from about 1.5 to about 4 grams.

In preferred embodiments, at least two of the films which form different compartments have different solubility, under the same conditions, releasing the content of the compositions which they partially or totally envelope at different times.

Controlled release of the ingredients of a multi-compartment pouch can be achieved by modifying the thickness of the film and/or the solubility of the film material. The solubility of the film material can be delayed by for example cross-linking the film as described in WO 02/102,955 at pages 17 and 18. Other water-soluble films designed for rinse release are described in U.S. Pat. Nos. 4,765,916 and 4,972,017. Waxy coating (see WO 95/29982) of films can help with rinse release. pH controlled release means are described in WO 04/111178, in particular amino-acetylated polysaccharide having selective degree of acetylation.

Other means of obtaining delayed release by multi-compartment pouches with different compartments, where the compartments are made of films having different solubility are taught in WO 02/08380.

Alternatively the dissolution of the liquid compartments can be delayed by modification of the liquid that is contained within the film. Use of anionic surfactants, particularly anionic surfactant mixtures that pass through a highly structured phase (such as hexagonal or lamellar) upon addition of water retards the dissolution of the surfactant containing compartment. In one aspect of this invention, one or more compartments comprise anionic surfactant and their release is delayed versus other compartments.

Auto-Dosing Delivery Device

The compositions of the invention are extremely useful for dosing elements to be used in an auto-dosing device. The dosing elements comprising the composition of the present invention can be placed into a delivery cartridge as that described in WO 2007/052004 and WO 2007/0833141. The dosing elements can have an elongated shape and set into an array forming a delivery cartridge which is the refill for an auto-dosing dispensing device as described in case WO 2007/051989. The delivery cartridge is to be placed in an auto-dosing delivery device, such as that described in WO 2008/053191.

EXAMPLES

Two automatic dishwashing compositions Composition 1 (low pH comprising anionic surfactant lime soap dispersant) and Composition 2 (high pH) were made as detailed herein below.

Test Method

An automatic dishwashing composition was made according to the below.

The tests carried out show the unexpected benefit of starch stain removal on dishware when a low temperature amylase was used in a low pH dishwashing composition containing a lime soap dispersant.

I. Preparation of Test Compositions

Tests were carried out using the following detergent compositions:

| Ingredient<br>Solid composition | Level (% wt)<br>Composition 1 |
|---|---|
| Sodium C$_{12-14}$ alkyl ethoxy 3 sulfate/ sodium carbonate particle (24.5% AE$_3$S and 52% sodium carbonate) | 20 |
| Citric acid | 30 |
| Sodium citrate | 20 |
| Sodium 1-hydroxyethylidene-1,1-diphosphonic acid | 10 |
| Sodium percarbonate | 10 |
| Suds suppressor agglomerate | 1 |
| 2-Pyridinol N-oxide | 8 |
| Processing Aids | Balance to 100% |

| Ingredient<br>Liquid composition | Level (% wt) |
|---|---|
| Lutensol ® TO 7 | 33 |
| Plurafac ® SLF180 | 27 |
| Lutensol ® FP 620 | 20 |
| Di propylene glycol | 15 |
| Glycerine | 1 |
| Processing Aids (aesthetics and water) | Balance to 100% |

A 1% solution of composition 1 in deionised water at room temperature had a pH of 6.5.

| Composition 2 | |
|---|---|
| Ingredient | Level (% wt) |
| Solid composition 2 | |
| Sodium triphosphate pentabasic | 56 |
| Sodium carbonate | 18 |
| Sodium percarbonate | 12 |
| Acusol ™ 588GF (sulfonated polymer supplied by DowChemical) | 9 |
| Tetraacetylethylenediamine | 4 |
| Sodium 1-hydroxyethylidene-1,1-diphosphonic acid | 1 |
| Zinc containing particle | 1 |
| Processing Aids | Balance to 100% |
| Liquid composition 2 | |
| Lutensol ® TO 7 (non-ionic surfactant supplied by BASF) | 41 |
| Plurafac ® SLF180 (non-ionic surfactant supplied by BASF) | 34 |
| Dipropylene glycol | 18 |
| Glycerine | 1 |
| Processing Aids (aesthetics and water) | Balance to 100% |

A 1% solution of composition 2 in deionised water at room temperature had a pH of 10.5.

The detergent compositions above contain no amylase enzyme—for the examples below amylase was added to these formulations as described.

II. Test Stains

The test stains used were 6.5 cm×10 cm melamine tiles soiled with mixed starch (DM277), supplied by the Centre for Testmaterials, Vlaardingen, The Netherlands.

III. Additional Ballast Soil

To add extra soil stress to the test, a blend of soils is added to the dishwasher, as prepared by the procedure described below

| Ingredient | % content |
|---|---|
| Potato Starch | 5.6 |
| Wheat Flour | 4.5 |
| Vegetable oil | 4.4 |
| Margarine | 4.4 |
| Lard | 4.4 |
| Single Cream | 9.0 |
| Baking Spread | 4.4 |
| Large Eggs | 9.0 |
| Whole Milk | 9.0 |
| Ketchup | 3.0 |
| Mustard | 4.0 |
| Benzoic acid >99% | 0.8 |
| Water (15-18 grains per US gallon) | 37.5 |
| Total | 100 |

Soil Preparation

1. Add water to the potato starch and leave to soak overnight. Then heat in a pan until the gel formed is properly inflated. Leave the pan to cool at room temperature overnight.
2. Weigh out the appropriate amounts of each ingredient.
3. Add the Ketchup and mustard to a bowl and mix vigorously until fully combined, 1 minute.
4. Melt Margarine, lard and baking spread individually in a microwave and allow to cool to room temperature then mix together.
5. Add Wheat Flour and Benzoic acid to a bowl and mix vigorously.
6. Break eggs into a bowl and mix vigorously.
7. Add vegetable oil to the eggs and stir using a hand blender.
8. Mix the cream and milk in a bowl.
9. Add all of the ingredients together into a large container and mix using a blender for ten minutes.
10. Weigh out 50 g batches of this mixture into plastic pots and freeze.

IV. Test Wash Procedure

| | |
|---|---|
| Automatic Dishwasher: | Miele, model 1022 |
| Wash volume: | 5000 ml |
| Water temperature: | 50° C. |
| Water hardness: | 15 grains per US gallon |
| Base detergent addition: | Added into the bottom of the automatic dishwasher after the initial pre-wash is complete. |
| Amylase enzyme addition: | Added into the bottom of the automatic dishwasher after the initial pre-wash is complete. |
| Additional ballast bottom rack: | 10x dinner plates<br>8x side plates<br>1x rectangular glass dish |
| Additional ballast top rack: | 2x small circular dishes<br>3x small tea cups |
| Positioning of spaghetti plates: | On bottom rack between 2x dinner plates. |
| Additional soil stress: | 50 g pot of frozen soil added to top rack. |

Example 1

One dose of detergent, comprising 8.59 g of the solid composition 1 or 16.25 g of solid composition 2, in both cases with 2 g of the liquid composition, and the amylase enzyme, where applicable, was added to the automatic dishwasher.

| Example | Composition |
|---|---|
| Formula A | Solid composition 2 + liquid composition + 0.72 mg Stainzyme Plus ® active enzyme protein. |
| Formula B | Solid composition 1 + liquid composition |
| Formula C | Solid composition 1 + liquid composition + 0.72 mg Stainzyme Plus ® active enzyme protein |
| Formula D | Solid composition 1 + liquid composition + 0.72 mg Termamyl ® active enzyme protein |

Tiles were removed every 5 minutes through the wash to monitor starch cleaning through time. Termamyl® is an amylase that falls outside the scope of the invention, whereas Stainzyme Plus® is a low temperature amylase of this invention.

The cleaning performance is shown in SRI. To calculate Stain Removal Index (SRI), Stain Removal Index (SRI) is defined as: 0=no removal at all, 100=complete removal and is assayed via image analysis.

| Time/minute | Detergent Stain Removal Index (SRI) | | | |
|---|---|---|---|---|
| | Formula A | Formula B | Formula C | Formula D |
| 5 | 0 | 0 | 0 | 0 |
| 10 | 0 | 0 | 0 | 0 |
| 15 | 9 | 0 | 2 | 0 |
| 20 | 25 | 0 | 8 | 0 |
| 25 | 39 | 0 | 50 | 0 |
| 30 | 57 | 0 | 74 | 0 |
| 35 | 63 | 0 | 76 | 4 |
| 40 | 67 | 1 | 77 | 13 |
| 45 | 74 | 5 | 85 | 12 |
| 50 | 72 | 4 | 89 | 12 |
| 55 | 76 | 8 | 86 | 8 |
| 60 | 72 | 7 | 86 | 15 |

As can be seen the composition of this invention (Formula C) offers superior and faster cleaning than the compositions that fall outside the scope of the invention (Formulas A, B and D).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

---

The invention claimed is:

1. A low-pH automatic dishwashing detergent composition comprising a low temperature tolerant amylase and from 2% to 10%, by weight, of a lime soap dispersing agent and wherein the composition has a pH as measured in 1% weight aqueous solution at 25° C. of from about 5 to about 6.5, wherein the amylase has 100% identity to SEQ ID NO:4 and further comprises substitutions at positions 9, 118, 149, 182, 186, 195, 202, 257, 295, 299, 320, 323, 339, 345, 458 and the deletions of D183* and G184*, wherein the lime soap dispersing agent comprises an alkyl ethoxysulfate surfactant and an alkoxylated polyalkyleneime, wherein the composition is builder free, wherein the amylase demonstrates at least 2 times the relative activity of a second amylase which has 100% identity to SEQ ID NO:3, wherein the lime soap dispersing agent has a lime scale dispersing power of no more than 8.

2. A composition according to claim 1 wherein the composition further comprises a suds suppressor.

3. A composition according to claim 1 wherein the lime soap dispersant can act as a soil swelling agent.

4. A composition according to claim 1 wherein the composition further comprises a crystal growth inhibitor.

5. A composition according to claim 1 wherein the composition further comprises a protease selected from the group consisting of:
   (i) a metalloprotease;
   (ii) a cysteine protease;
   (iii) an aspartate protease, and
   (iv) mixtures thereof.

6. A composition according to claim 1 wherein the composition further comprises at least one further enzyme selected from the group consisting of a pullulanase, a lipase, a cellulase, an oxidase, a phospholipase, a perhydrolase, a xylanase, a pectate lyase, a pectinase, a galacturanase, a hemicellulase, a xyloglucanase, a mannanase and mixtures thereof.

7. A composition according to claim 1 wherein the composition further comprises a buffer.

8. A composition according to claim 1 wherein the composition further comprises an iron chelant wherein the iron chelant is selected from the group consisting of siderophores, catechols, enterobactin, hydroxamates, hydroxypyridinones (or hydroxypyridine N-Oxides) and mixtures thereof.

9. A composition according to claim 1 wherein the composition further comprises an iron chelant selected from the group consisting of 1,2-dihydroxybenzene-3,5-disulfonic acid, 2-pyridinol 1 oxide and mixtures thereof.

10. A composition according to claim 1 wherein the composition comprises less than about 5% by weight of the composition of bleach.

11. A composition according to claim 1 comprising a metalloprotease, an anionic surfactant, a dispersing polymer and a crystal growth inhibitor.

12. A single or multi-compartment water-soluble cleaning pack comprising a cleaning composition according to claim 1 and a water-soluble enveloping material wherein the weight of the pack is from 5 to 40 g.

13. A method of cleaning dishware/tableware in an automatic dishwasher comprising the step of subjecting the ware to a wash liquor comprising a composition according to claim 1.

* * * * *